(12) United States Patent
Lu et al.

(10) Patent No.: US 6,861,512 B2
(45) Date of Patent: Mar. 1, 2005

(54) SEPARATION OF OLEFINIC ISOMERS

(75) Inventors: Lily Lu, Bedford, MA (US); John D. Orr, Amesbury, MA (US)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/798,020

(22) Filed: Mar. 1, 2001

(65) Prior Publication Data

US 2002/0019521 A1 Feb. 14, 2002

Related U.S. Application Data

(60) Provisional application No. 60/186,269, filed on Mar. 1, 2000.

(51) Int. Cl.$^7$ .......................... C07G 3/00; C07H 15/00; C07H 17/00
(52) U.S. Cl. ................... 536/18.5; 536/17.1; 536/17.2; 536/18.7; 536/55; 536/55.2; 536/124; 536/127; 536/123.13
(58) Field of Search ............................... 536/17.1, 17.2, 536/18.5, 18.7, 55, 55.2, 124, 127, 123.13, 1.11; 554/1, 175

(56) References Cited

U.S. PATENT DOCUMENTS

| | | | |
|---|---|---|---|
| 3,940,972 A | * | 3/1976 | Norell et al. ................ 72/23.1 |
| 5,569,808 A | | 10/1996 | Cansell et al. |
| 5,681,824 A | | 10/1997 | Christ et al. |
| 5,750,664 A | * | 5/1998 | Christ et al. ............... 536/17.2 |
| 5,843,918 A | | 12/1998 | Christ et al. |

OTHER PUBLICATIONS

Bhat et al. J. of Chromatography, 260 (1983) 129–136.*
Scacchi et al. J. of Chromatography, 114 (1975) 255–257.*
Grindel et al. J. of Chromatography, 272 (1983) 210–215 (Abstract).*
Bhat, Pangala V. et al., "Effect of 2-Alkanols on the Separation of Geometric Isomers of Retinol in Non-Aqueous High-Performance Liquid Chromatography" Journal of Chromatography 260:129–136 (1983).

Creer, Michael H. et al., "Separation of Isomeric Lysophospholipids by Reverse Phase HPLC", Lipids 20:922–928 (1985).
Dimitrova, B.A., HPLC Method for Separation of Trans/CIS Isomers of Unsaturated Hydrocarbons Using a Silver Nitrate Impregnated Silica Gel (10 $\mu$m), Comptes rendus de l'Academie bulgares des Sciences, Tome 32, N 10:1381–1384 (1979).
Eisen, Heliu Raude, O., "Separation and Preparative Purification of Geometric Isomers of $C_9$–$C_{12}$n–Alkenes by Gas Chromatography, Using $AgNO_3$ and Hexandiol–1,6 as a Stationary Phase", Eesti NSV Teaduste Akadeemia Toimetised, 198 Koide Keemia Geoloogia: 168–170 (1970).
Köhler, J. et al., "Preparative LC Separation and Isolation of Enantiomerically Pure Olefins", Chromatographia 18:119–124 (1984).
Magidman, R.A. et al., "Bound–Monolayer Cation Exchanger for Gas–Liquid Chromatographic Separation of cis and trans Alkenes", Analytical Chemistry 48:44–47 (1976).
Moberg, Christine et al., "Ligand–exchange Chromatography of Alkenes on Stationary Phases Containing Palladium(II) Complexes, Enantiomeric Separation of trans–1, 2–divinylcyclohexane" Journal of Chromatography 585:309–314 (1991).
Scacchi, G. et al., "Separation and Analysis of Small Quantities of Saturated $C_6$ Hydrocarbons from Large Quantities of Olefins", Journal of Chromatography 114:255–257 (1975).
Schomburg G., et al. "Separation of Olefinic Compounds by Reversed–phase Liquid Chromatography with a Mobile Phase Containing $\pi$–Complexing Metal Salts Like Silver Nitrate" Journal of Chromatography 114:147–178 (1975).

* cited by examiner

Primary Examiner—James O. Wilson
Assistant Examiner—Patrick T. Lewis
(74) Attorney, Agent, or Firm—Wilmer, Cutler, Pickering, Hale and Dorr LLP

(57) ABSTRACT

The geometric isomers of olefins and olefinic compounds are separated by means of liquid chromatography using a stationary phase comprising an organosilane with a pendant aliphatic functional group such as $C_{18}$ and a mobile phase which includes an additive comprising alkanes and alkenes.

18 Claims, 11 Drawing Sheets

SEPARATION OF OLEFINIC ISOMERS

This application claims benefit of 60/186,269 Mar. 1, 2000.

FIELD OF THE INVENTION

This invention is in the field of liquid chromatography and relates to methods of separating cis and trans carbon-carbon double bond isomers.

BACKGROUND OF THE INVENTION

In the synthesis of compounds with a carbon-carbon double bond, otherwise known as olefins or alkenes, typically, only one isomer (cis or trans) is desired. Syntheses are typically designed to produce only one isomer. However, a small amount of the undesired isomer is often produced. It is important to quantify the levels of all such undesired isomers as well as all other impurities in drug substance batches. One type of undesired isomer, in olefinic drug substances, is carbon-carbon double bond isomers. In order to quantify the levels of all drug substance-related impurities in drug substance batches, all impurities require analysis by an impurity assay.

Liquid chromatography is currently recognized as the most promising technology to achieve separation between carbon-carbon double bond isomers. Application of high pressure liquid chromatography (HPLC) techniques, in particular, for the separation of some isomers of carbon-carbon double bond compounds has in the past met with frustration, primarily due to the fact that it has been, heretofore, difficult to effect a satisfactory level of separation of cis and trans isomers that are structurally identical except for the geometric configuration of the carbon-carbon double bond. Although the prior art discloses various methods of separating cis and trans isomers using liquid or other chromatographic means, none has achieved a consistent and stable means for effecting separations in a reliable and reproducible manner for analytical and preparative uses.

Thus there still remains the continuing need to develop a liquid chromatography system to effectively separate cis and trans isomers of carbon-carbon double bond compounds.

SUMMARY OF THE INVENTION

This invention is directed to a method for the separation of geometric isomers from mixtures containing both cis and trans forms of carbon-carbon double bond-containing compounds using liquid chromatography.

To separate cis and trans isomers of geometric isomer mixtures, the method of this invention involves flowing a mobile phase through a column means containing a stationary phase comprising an organosilane with a pendant aliphatic functional group attached to a solid support, where the mobile phase includes a geometric isomer mixture and an aliphatic hydrocarbon, with the aliphatic hydrocarbon being capable of adsorbing to the pendant aliphatic functional group and preferentially interacting with the isomers to resolve the mixture into its cis and trans components and thus to effect the separation of the desired isomer from the mobile phase as an effluent stream and collecting a first portion of the eluent stream substantially comprising the cis isomer; and collecting a second portion of the effluent stream containing the trans isomer.

This invention also directed to a method for analyzing a mixture containing geometric isomers of an olefinic compound having an acid or phosphate functional group comprising flowing a mobile phase through a column means containing a stationary phase. The stationary phase comprises an organosilane having a pendant aliphatic functional group attached to a solid support. The mobile phase comprises a geometric isomer mixture of an olefinic compound and at least one aliphatic hydrocarbon. The aliphatic hydrocarbon comprises an alkane or alkene having the formula $C_nH_{2n+2}$ and $C_nH_{2n}$, respectively, where n=4 to n=16. The aliphatic hydrocarbon preferentially interacts with the isomers in the mobile phase to effect the separation of the desired isomer from the mobile phase as a column effluent stream. A property of the column effluent which is representative of changes in composition thereof is measured.

The invention is more specifically directed to methods for separating a mixture containing geometric isomers of olefins or olefinic compounds using alkanes and alkenes in the mobile phase, where the isomerism occurs as cis and trans conformations of an aliphatic hydrocarbon side chain.

This invention is further directed to a method of analyzing a geometrical isomer mixture to elute sequentially the olefinic constituents of the sample, and measuring a property of the column effluent which is representative of changes in composition thereof.

By using the method of this invention, a quantitative determination can be made of each of these isomers from geometric mixtures thereof.

DETAILED DESCRIPTION OF THE INVENTION

Figure 1:
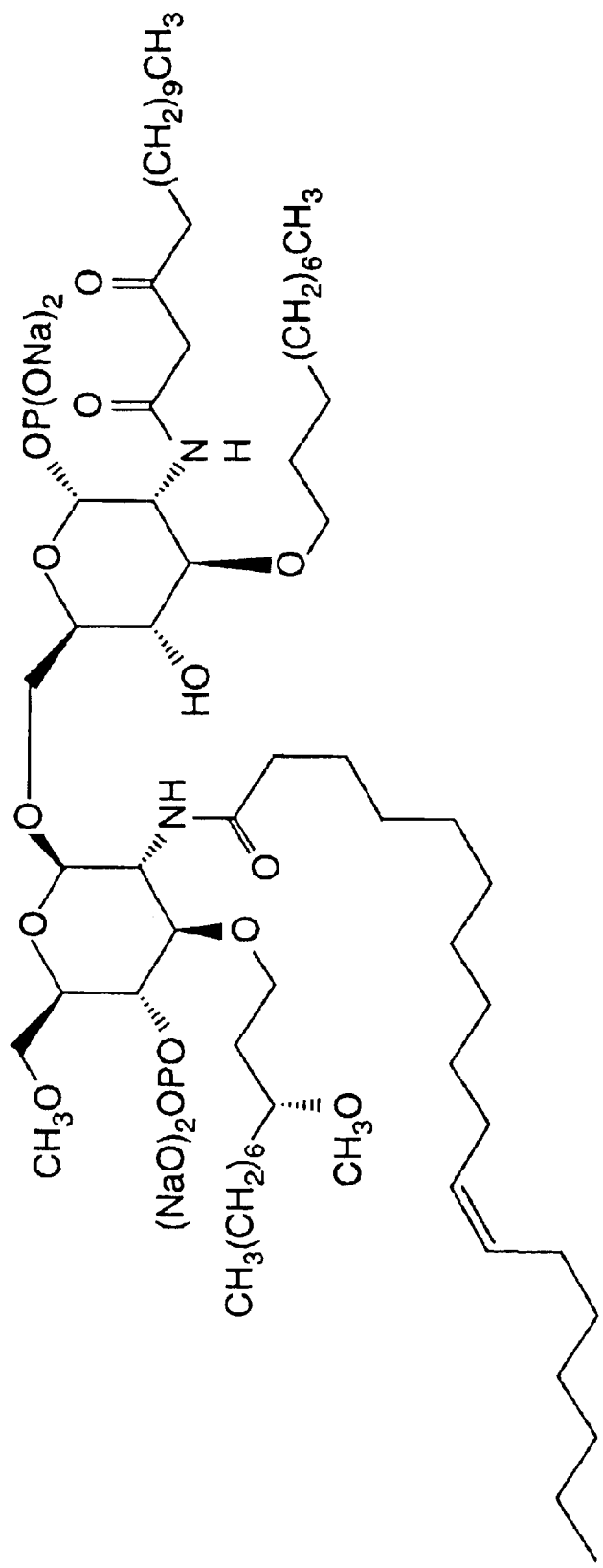
FIG. 1 is a structural formula for the cis-isomer of a substituted liposaccharide, E5564.

The patent applications, patents, and literature references cited herein indicate the knowledge of those of ordinary skill in this field and are hereby incorporated by reference in their entirety. In the case of inconsistencies between any reference cited herein and the specific teachings of the present disclosure, this disclosure will prevail.

The present invention discloses methods for separating a mixture containing geometric isomers of a double carbon-carbon bond compound using liquid chromatography techniques. Moreover, this invention provides a quick and simple chromatographic means for determining levels of impurities, such as an undesired isomeric form, in drug substance batches of olefinic compounds. Marked differences in pharmacological selectivity, efficacy, and biological activity have been observed between the cis and trans forms of pharmaceutical compositions. For that reason, it is important to have a reliable and reproducible method for separating the cis and trans forms of geometric isomers.

As used herein, the term "geometric isomers" refers to the term as generally understood by one of ordinary skill in the art and as discussed in the standard chemical text, Morrison and Boyd, *Organic Chemistry* (6$^{th}$ ed. 1992).

The carbon-carbon double bond-containing compounds that can be separated in the methods of this invention are generally referred to as olefins and olefinic compounds. Olefins and olefinic compounds include, but are not limited to, substituted liposaccharides (including but not limited to those disclosed in U.S. Pat. No. 5,681,824 and the structure shown in FIG. 1), alkenoic acids (which as used herein, include a family of compounds, including but not limited to, octadecenoic acid), retinoids (which as used herein include a family of compounds, including but not limited to, retinoic acids, retinals, and retinols), and carotenoids (which as used herein include a family of compounds, including, but not limited to, carotenes).

By use of this invention, a separation of the cis and trans forms of compounds containing a plurality of long aliphatic side chains can be achieved where the structural difference in the cis and trans forms of the isomers occurs in one carbon-carbon double bond bearing chain. As used herein, the term "separation" refers to partial and/or substantially complete resolution of cis and trans isomers sufficient for qualitative and/or quantitative analysis of a compound sample, and/or physical isolation of a desired isomer eluent that is substantially free of the undesired isomer.

By way of illustration, but not intended to be limiting, the following substituted liposaccharide, useful in treating endotoxemia, and which is the subject of U.S. Pat. No. 5,681,824, which is hereby incorporated by reference in its entirety, can exist as both a cis and trans isomer. One representative structure of the cis-double bond isomer of the substituted liposaccharide of U.S. Pat. No. 5,681,824, is provided in FIG. 1. Other representative structures include compounds of the formula:

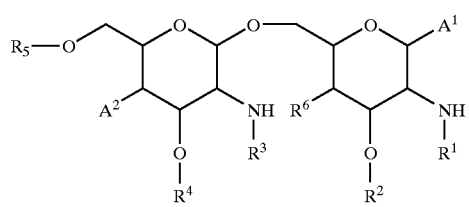

where $R^1$ is selected from the group consisting of

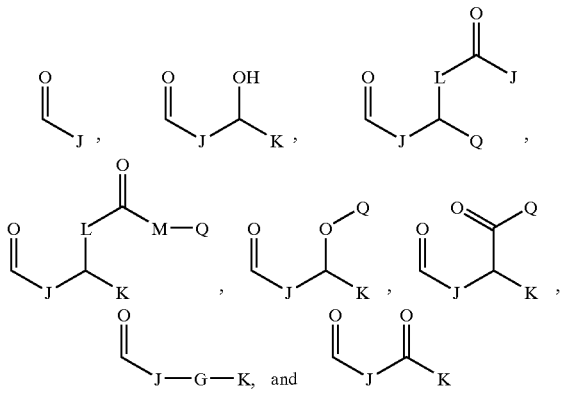

where each J, K and Q, independently, is straight or branched C1 to C15 alkyl; L is O, NH or $CH_2$; M is O or NH; and G is NH, O, S, SO, or $SO_2$;

$R^2$ is straight or branched C5 to C15 alkyl;

$R^3$ is selected from the group consisting of

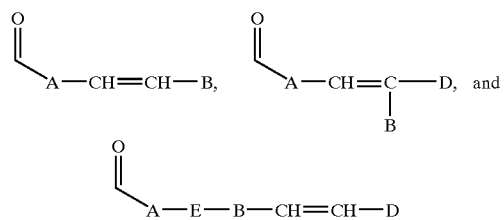

where E is N, O, S, SO or $SO_2$; each A, B and D, independently, is straight or branched C1 to C15 alkyl;

$R^4$ is selected from the group consisting of straight or branched C4 to C20 alkyl, and

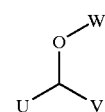

where each U and V, independently, is straight or branched C2 to C15 alkyl and W is hydrogen or straight or branched C1 to C5 alkyl;

$R^5$ is selected from the group consisting of hydrogen, J',-J'-OH, -J'-O—K',-J '-O—K'—OH, and -J'—O—PO $(OH)_2$, where each J' and K', independently is straight or branched C1 to C5 alkyl;

$R^6$ is selected from the group consisting of hydroxy, halogen, C1 to C5 alkoxy and C1 to C5 acyloxy;

$A^1$ and $A^2$, independently, are selected from the group consisting of

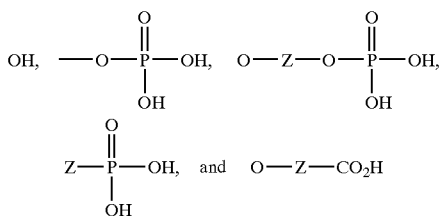

where Z is straight or branched C1 to C10 alkyl; or pharmaceutically acceptable salts thereof.

This structure is merely one example, and other substituted liposaccharides are within the scope of this invention.

With reference to FIG. 1, the terminal eight carbon portion of the carbon-carbon double bond bearing side chain may exist in the cis position, as shown in FIG. 1, or in the trans position. Other than the small structural difference that occurs in the olefinic side chain, the cis and trans isomers may otherwise be chemically identical. Thus, purification of the cis isomer from the less desired trans isomer using general chromatographic separation techniques has posed special challenges.

While there are a number of separation techniques, the methods of this invention may be accomplished using chromatography, for example, high-performance liquid chromatography (HPLC), supercritical fluid chromatography (SEC), or capillary electrochromatography (CEC).

The above listed techniques are merely representative, and other alternative and more recently developed chromatographic means are within the scope of the invention. In brief, SFC is similar to HPLC and comprises a column, an injector, a pump, a column temperature controlling device, a detector (UV or flame ionization detector, typically), a recording device, and an electronic system controlling device (computer). The mobile phase, however, comprises a supercritical fluid such as carbon dioxide, $N_2O$, alkanes, or ammonia.

Capillary electrochromatography (CEC) is another separation technique which combines the properties and advantages of capillary electroosmotic flow with the separation selectivity of liquid chromatography. Capillary electrochromatography is a hybrid technology combining aspects of capillary electrophoresis and liquid chromatography. CEC separates charged or ionic and neutral substances by electroosmotic flow, and the substances are eluted through capillary columns using a liquid mobile phase. The CEC system typically consists of an injector, a CEC column that is typically 100 μm (microns) in internal diameter, 30–50 cm in length, packed with a 3 μm particle size $C_{18}$ packing material, e.g. Hypersil, an air pump for pressurizing liquids for column solvent delivery and flushing, electrodes placed in buffers at either end of the capillary column, a column temperature controlling device, a detector (UV, typically), a recording device, and an electronic system controlling device (computer).

HPLC, the preferred chromatography method, is a technique that utilizes a stationary phase and a mobile phase to effect separation of a geometric isomer mixture. In this technique, a mobile phase flows through a column containing a stationary phase which selectively adsorbs components of interest from the geometric isomer mixture in a mobile phase, such that the isomers are separated.

By column means is meant a packed column or any standard stationary phase container which may be used in column liquid chromatography separations. The column means is packed with very fine particles as column packing material, and constitutes the stationary phase which effects the separation of liquid components.

By stationary phase is meant the solid support material, typically small inorganic and/or organic particles, in the column means that selectively adsorbs or absorbs components of interest from the geometrical isomer mixture in a mobile phase. Particle sizes of analytical HPLC column packings currently typically range from about 1 to about 10 μm in size, with a preferred size of about 3–5 μm; preparative HPLC column packings range in size from about 5 to about 350 μm in size, preferably about 200 μm.

In the method of this invention for separating geometric isomers organic compounds, the stationary phase is a solid material including but not limited to silica, polystyrene, alumina, or preferably, organosilanes that contain a pendan functional group that is attached to an inorganic support. This pendant functional group, such as $C_{18}$, or $C_{30}$, is ideally sufficiently removed from the surface of the support so at it may interact with the mixture of components in the mobile phase. A preferred stationary phase includes organosilanes that covalently bind the pendant functional groups to the core support while holding the pendant functional group sufficiently distant from the surface of the core support so as to permit approximating the physical and chemical properties the functional group would exhibit under homogeneous conditions. These organosilanes are derived from materials which are characterized as having the property to react with surface hydroxy groups of the core support to form oxygen-silicon bond(s), i.e. all have the ability to silylate the core supports. It is to understood that any such organosilanes with a variety of pendant aliphatic functional groups may be employed, and that the present invention is not necessarily limited thereto. This invention employs any such organosilanes bound to aliphatic functional group(s).

In the preferred method of this invention, the core stationary support comprises a network of silica and oxygen atoms with hydroxy groups that may be alkylated beyond the core structure. As one of ordinary skill in the art will appreciate, stationary supports are readily available commercially. See Waters Chromatography Columns and Supplies Catalog 1999–2000, page 54. HPLC columns are available in a variety of column lengths (typically about 30–300 mm) and diameters (typically about 0.5 to 20 mm). Typical silica-based packings include amino, cyano, phenyl, strong cation exchange, strong anion exchange, methyl ($C_1$), butyl ($C_4$), hexyl ($C_6$), octyl ($C_8$), octadecyl ($C_{18}$) and carotenoid ($C_{30}$) as the pendant functional group.

For the purposes of this invention, the $C_{18}$ and $C_{30}$ columns are preferred. The $C_{18}$ and $C_{30}$ columns contain carbon chains which are covalently bound to a surface of the core solid support, and which termini are able to associate with the mobile phase and analytes therein.

By mobile phase is meant the eluent which will flow through the column means containing the stationary phase, and which works in combination with the stationary phase such that the combination is capable of separating the cis and trans isomers of the geometrical isomer mixture. The mobile phase may comprise methanol and/or other solvents and modifiers including but not limited to, acids, bases, and chiral separation agents. For the mobile phase of the method of this invention, short-chain aliphatic hydrocarbons including alkanes and alkenes having the formula $C_nH_{2n+2}$ and $C_nH_{2n}$, respectively, where n=4 to n=16, preferably 6–12, are used as the mobile phase modifier. Other components of the mobile phase preferably comprises, but are not limited to, methanol, water and phosphoric acid. It is preferred to use $C_6$–$C_{12}$ alkenes to resolve the cis and trans isomeric forms when added to the mobile phase. The selection of which short chain aliphatic hydrocarbon as defined above to use will depend upon the geometrical isomer being separated and the HPLC conditions being used.

Using the methods described herein, one of skill in the art can routinely evaluate which mobile phase component will achieve the best separation of the cis and trans isomers. Although not wishing to be bound by the following statement, it is theorized that the separation is achieved by differentials in the π—π interaction, van der Waals interactions, and other interactions between the mobile phase modifier, e.g. 1-dodecene, and the cis and trans aliphatic chains of the olefinic compounds.

Additional and optional elements can include, but are not limited to, means for degassing the mobile phase, filtration systems, high pressure pumps, pressure gauges, means for controlling the temperature of the columns, detectors, fraction collectors and electronic and/or computer recording and control devices. Additionally, preparative HPLC can similarly be accomplished by using higher capacity columns to accommodate the higher sample sizes usually employed.

By resolution is meant at least a partial and/or substantially complete separation of individual cis and trans geometric isomers contained in a mixture sufficient for analytical and/or preparative purposes using any separation means. A theory used to describe such separation by contacting a mobile phase with a stationary phase involves the repeated adsorption or absorption and deadsorption or deabsorption of the components of a mixture with the stationary phase. Under this theory, the components of the mixture traveling in the mobile phase come into contact with and are adsorbed or absorbed by the stationary phase, and, subsequently are deadsorbed or deabsorbed from the stationary phase to travel once again in the mobile phase until they contact another part, or a successive stage, of the stationary phase. Different components are preferentially adsorbed or absorbed and deadsorbed or deabsorbed which results in the separation of the components.

The olefinic constituents of the geometric isomer mixture that are sequentially eluted are analyzed by measuring a property of the column effluent which is representative of changes in composition thereof. As understood by one of ordinary skill in the art, any means of measuring changes in composition including typical detection means such as UV, refractive index, evaporative light scattering, or mass spectrometric detectors are within the scope of the invention.

The following Examples will further illustrate the invention. The Examples are not intended, and should not be interpreted, to limit the scope of the invention which is more fully defined in the claims which follow.

EXAMPLE 1

Separation of Isomers Using Carotenoid $C_{30}$ HPLC Columns

Two separate $C_{30}$ HPLC columns were tested for their ability to separate the compound of FIG. 1 from its trans isomer (specifically denoted, E5564, and B1444, respectively) as well as other impurities contained in a Sample A without the use of mobile phase additives. Identical HPLC conditions were used for the testing of each column.

The HPLC columns that were utilized, YMC Carotenoid $C_{30}$ columns, are commercially available and are specifically marketed as useful for separating carbon-carbon double bond compounds. Each $C_{30}$ HPLC column (YMC Carotenoid $C_{30}$, 250×4.6 mm, 5 μm particle size, 300 Å pore size) was affixed to a Hewlett Packard 1050 HPLC system and maintained at ambient temperature. The HPLC system was comprised of an autosampler fitted with a 0.1 to 100 μL viable sample loop, a solvent delivery system (e.g. ternary pump), utilizing low-pressure mixing, and a variable wavelength detector set at 254 nm. The HPLC system was controlled by a personal computer operating Hewlett Packard ChemStation software version 03.02 for HPLC.

Two solvents were used in this gradient HPLC method. Solvent A was composed of 980 mL of water and 20 mL of phosphoric acid. Solvent B was composed of 980 mL of methanol and 20 mL of phosphoric acid. Methanol of HPLC grade was purchased from J. T. Baker, Phillipsburg, N.J., USA; water was purified by double reverse osmosis then end-polished by a US Filter Modulab™ water purification system; and phosphoric acid (85 weight %, iron content below 1 part per billion) of biochemical grade was purchased from Wako Chemical, Richmond, Va., USA.

The method run time was 70 minutes, and column re-equilibration time was 20 minutes. The flow rate was constant at 0.7 mL/min. A simple linear gradient was used. The initial conditions were 10% solvent B and 90% solvent A. They were changed from 10% to 100% solvent B, linearly, from initial time to 40 minutes thereafter. The final gradient condition, 100% solvent B, was maintained from 40 until 70 minutes.

A sample was prepared by transferring 25 mg of a compound sample comprising the compound of FIG. 1, and various other impurities, including the trans isomer of the compound of FIG. 1 ("Sample A"), to a 5 mL volumetric flask, diluting to 50–80% volume with methanol and mixing until dissolved. The flask was diluted to volume, mixed by inversion, and a portion of the solution was transferred to an amber HPLC vial and capped. The blank (control) sample was methanol. As used herein, a blank or control sample comprises a solvent that comprises a diluent without the addition of the analyte (i.e. material being analyzed). For analyses, 25 μL of Sample A were injected into the HPLC system.

Figure 2:
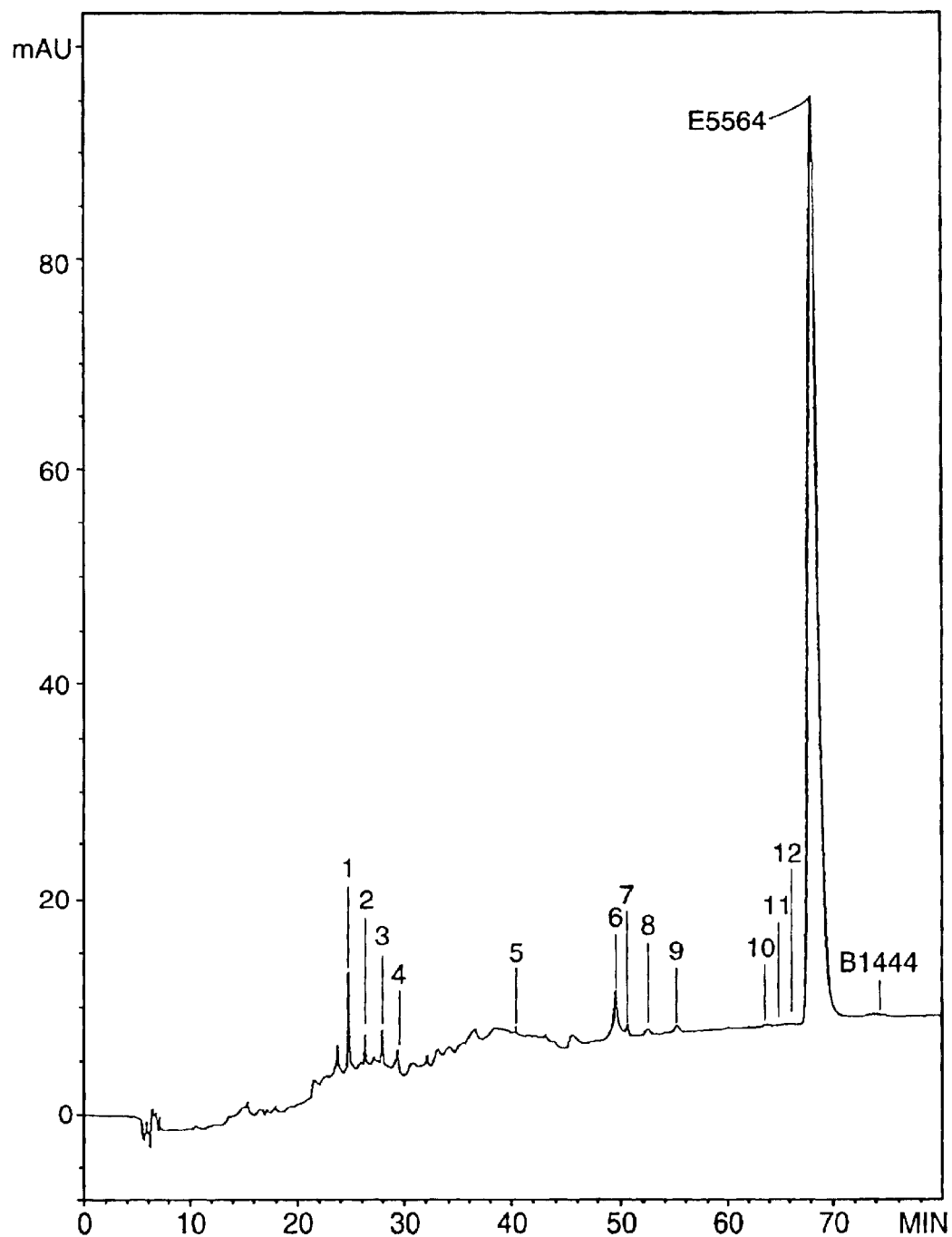
FIG. 2 is a Carotenoid $C_{30}$ HPLC column chromatogram of a sample drug substance batch showing the presence of the compound of FIG. 1, E5564, its trans isomer, B1444, and various impurities numbers 1 through 12.

FIG. 2 is a representative chromatogram for one of the Carotenoid $C_{30}$ HPLC columns, Column Number 144 (Eisai Research Institute-Chemical Development Column Number 144), that were tested. As shown in FIG. 2, the column allowed for the separation and quantification of impurities 1–12, in addition to B1444. While impurities 10, 11, and 12 were difficult to observe at the magnification shown, they were indeed detectable. The other baseline disturbances shown in FIGS. 2 and 3, were also present in the blank (control) samples and therefore do not constitute impurity peaks present in Sample A.

Figure 3:
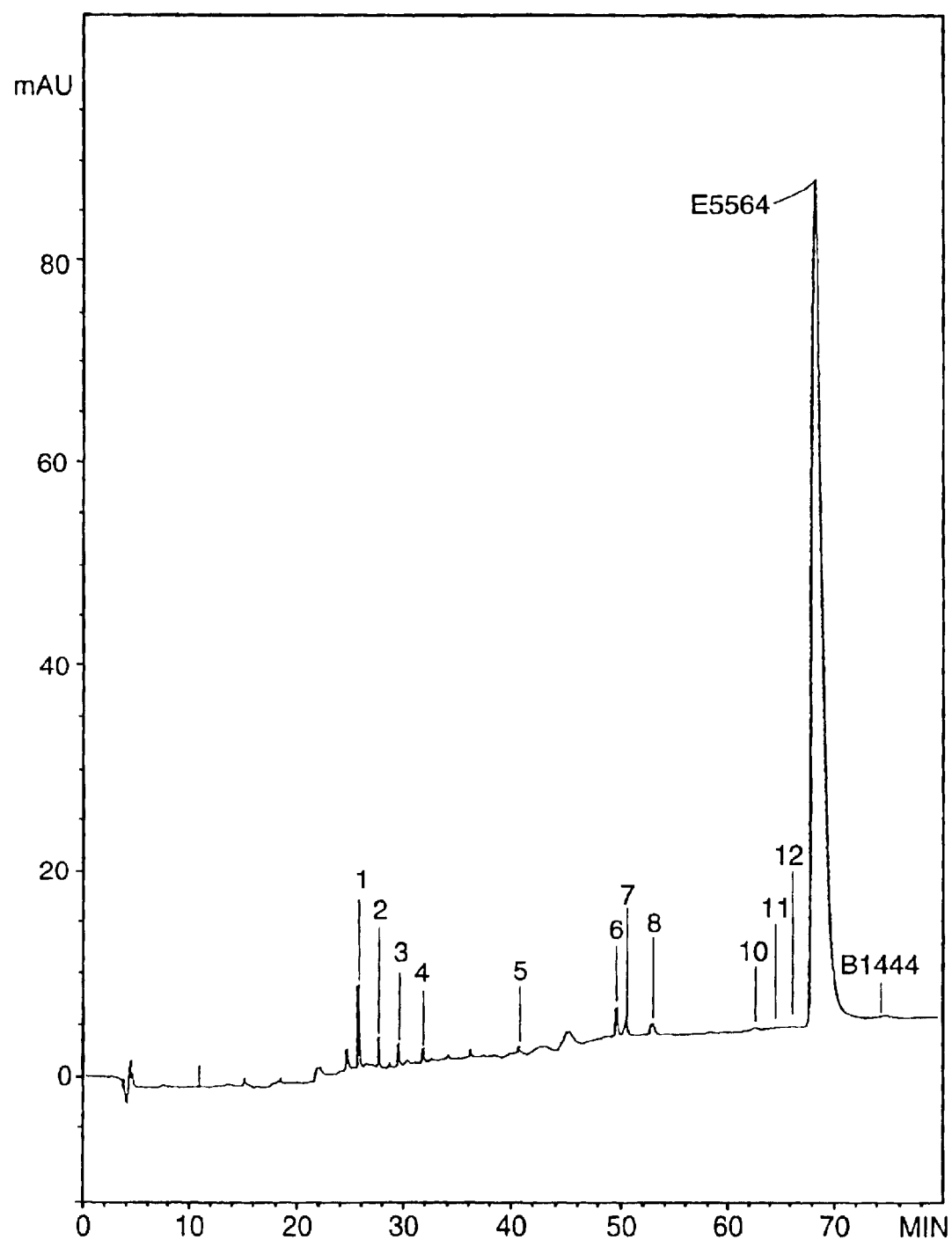
FIG. 3 is a Carotenoid $C_{30}$ HPLC column chromatogram of a sample drug substance batch identical to that used for the chromatogram of FIG. 1, but which fails to show the presence of impurity number 9.

A serious analytical shortcoming of the Carotenoid $C_{30}$ HPLC column for the separation of the cis and trans isomers of FIG. 1 is illustrated in FIG. 3. Use of Carotenoid $C_{30}$ HPLC Column Number 145 (Eisai Research Institute-Chemical Development Column Number 145) did not allow for the observation of impurity 9. It was known from the use of Carotenoid $C_{30}$ HPLC Column Number 144 (and other Carotenoid $C_{30}$ HPLC columns) that impurity 9 was indeed present in Sample A. Thus, since use of Carotenoid $C_{30}$ HPLC Column Number 145 failed to allow for the observation of impurity 9 which is known to be present in Sample A, it was determined that the Carotenoid $C_{30}$ HPLC column, although specifically marketed for the separation of olefinic isomers, was unacceptable as a tool for the purification and analysis of Sample A. Such lot to lot variability between the two columns tested demonstrated that the Carotenoid $C_{30}$ HPLC column could not be relied upon for analyses of drug substance batches.

Thus, although it was determined that a $C_{30}$ HPLC column may subtantially resolve the cis and trans forms of the compound without the need of a mobile phase modifier, an unacceptable level of variability in the resolution was observed in the lots tested. Furthermore, one lot of the $C_{30}$ columns tested failed to detect and separate other impurities in the isomer mixture. Thus, it was determined that $C_{30}$ was acceptable as a general analytical method for the separation of the compound of FIG. 1 and its trans isomer.

EXAMPLE 2

Separation of Isomers Using 1-Octene as Mobile Phase Additive

The effects of the presence of 1-octene in the mobile phase on the separation of the E5564 (cis isomer), as shown in FIG. 1, from its trans double bond isomer, B1444, were examined, with and without 1-octene in the mobile phase. Other than for the composition of the mobile phase, each trial was conducted under the same HPLC conditions. The first method utilized a mobile phase that did not contain 1-octene (see FIG. 4).

A. Control

A $C_{18}$ HPLC column (YMC-Pack ODS-AP 303, 250×4.6 mm, 5 µm particle size, 300 Å pore size; YMC catalog number AA30S05-2546WT) was affixed to a Hewlett Packard 1090 HPLC system and maintained at 20–25° C. The HPLC system was comprised of an autosampler fitted with a 0.1 to 100 µL variable sample loop, a pump (solvent delivery system), utilizing high-pressure mixing, and a diode array detector set at 254 nm. The HPLC system was controlled by a computer operating Hewlett Packard ChemStation software version 03.02 for HPLC.

Figure 4:
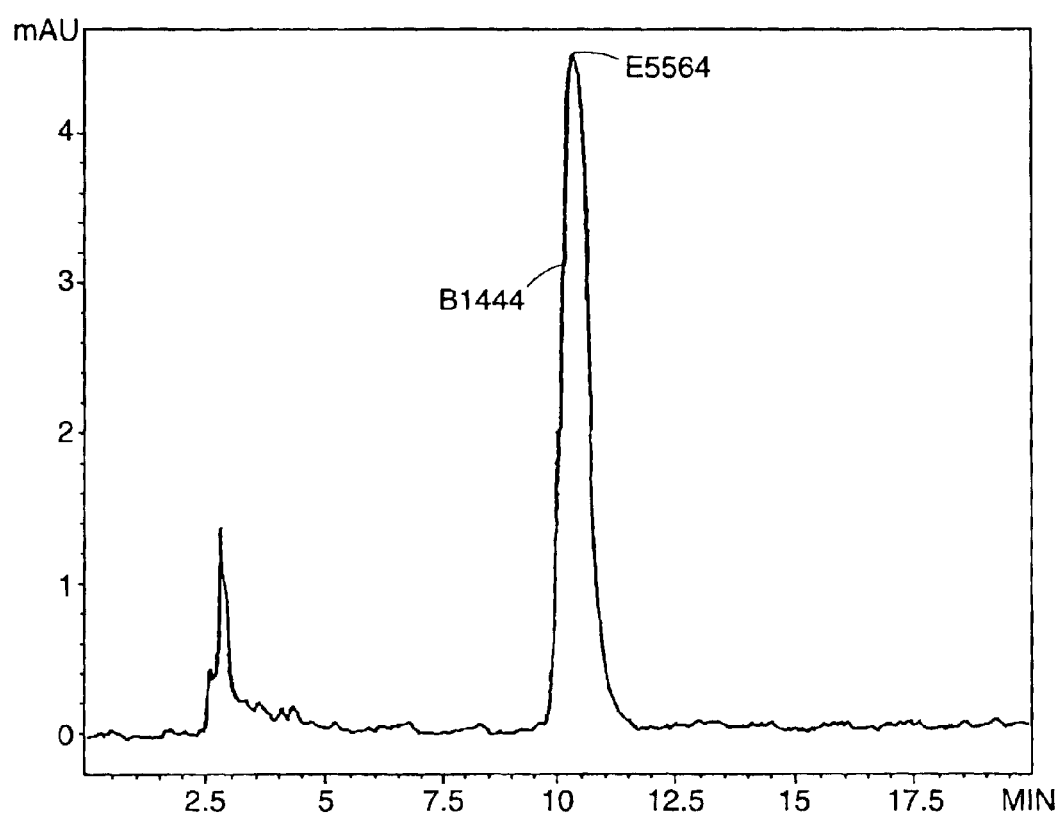
FIG. 4 is an HPLC chromatogram of the compound of FIG. 1 and its trans isomer using 2% by volume of phosphoric acid in methanol in the mobile phase in a $C_{18}$, column.

The data shown in FIG. 4 was generated by eluting the HPLC column with 2% by volume of phosphoric acid and 98% by volume of methanol. HPLC-grade methanol was purchased from J. T. Baker, Phillipsburg, N.J., USA; water was purified by double reverse osmosis then end-polished by a US Filter Modulab™ water purification system; and biochemical-grade phosphoric acid (85 weight-%, iron content below 1 part per billion) was purchased from Wako Chemical, Richmond, Va., USA.

A sample was prepared by transferring 5 mg of the E5564 (cis isomer) and 4 mg of the B1444 (trans double bond isomer of E5564) to an amber HPLC vial, adding 1 mL methanol, capping and mixing until dissolved by hand vortexing. For analyses, 25 µL were injected into the HPLC system.

Referring to FIG. 4 of the drawings, the separation of E5564 from its trans double bond isomer, B1444, was tested on a $C_{18}$ HPLC column (specifically, YMC ODS AP-303, 4.6×250 mm, 5 µm packing, 300 Å pore size) using 2% by volume of phosphoric acid in methanol as the mobile phase. As shown in FIG. 4, the only evidence of partial resolution was a slight shoulder on the peak which eluted at about 10.5 minutes.

B. 1-Octene

Figure 5:
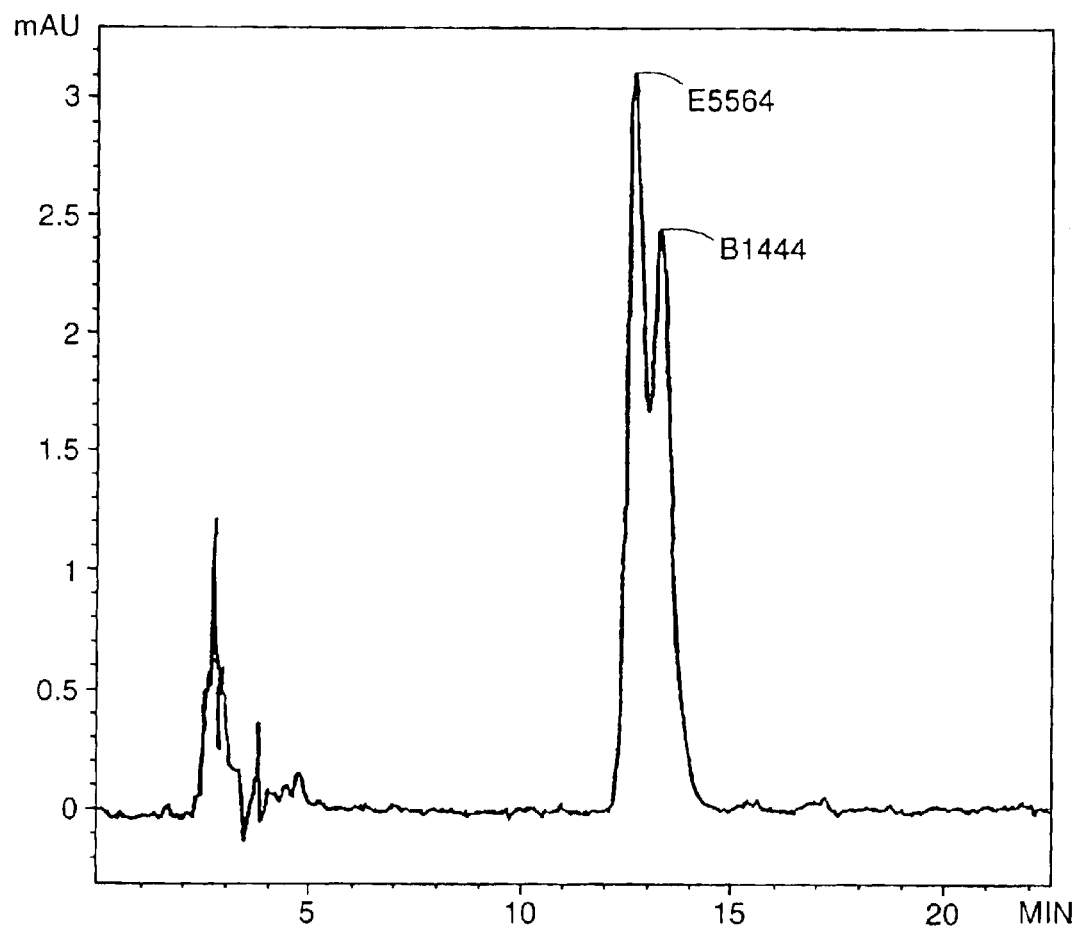
FIG. 5 is an HPLC chromatogram of the compound of FIG. 1 and its trans isomer using 2% by volume of phosphoric acid, 3% by volume of water, and 5% by volume of 1-octene in methanol in the mobile phase in a $C_{18}$ column.

In comparison, and as shown in FIG. 5, when the same procedure as described for the control was employed, but using 5% 1-octene in methanol in the mobile phase, the resolution of the isomers improved dramatically, with the cis isomer, E5564, eluting at a retention time of about 12.5 minutes, and the trans isomer eluting at about 13.5 minutes.

A $C_{18}$HPLC column (YMC-Pack ODS-AP 303, 250×4.6 mm, 5 µm particle size, 300 Å pore size; YMC catalog number AA30S05–2546WT) was affixed to a Hewlett Packard 1090 HPLC system and maintained at 20–25° C. The HPLC system was comprised of an autosampler fitted with a 0.1 to 100 µL variable sample loop, a pump (i.e., a type of solvent delivery system), utilizing high-pressure mixing, and a diode array detector set at 254 nm. The HPLC system was controlled by a computer operating Hewlett Packard ChemStation software version 03.02 for HPLC. The procedure was isocratic, with a flow rate of 1.2 mL/min, and a run time of 20 minutes.

The HPLC column was eluted with a mobile phase comprising phosphoric acid, water, 1-octene, and methanol (2%, 3%, 5%, and 90% by volume, respectively). HPLC-grade methanol was purchased from J. T. Baker, Phillipsburg, N.J., USA; water was purified by double reverse osmosis then end-polished by a US Filter Modulab™ water purification system; phosphoric acid (85 weight-%, iron content below 1 part per billion) of biochemical grade was purchased from Wako Chemical, Richmond, Va., USA; and 1-octene of 99+% purity was purchased from Acros Organics/Fisher Scientific, New Jersey, USA.

A sample was prepared by transferring 5 mg E5564 and 4 mg B1444 (trans double bond isomer of E5564) to an amber HPLC vial, adding 1 mL methanol, capping and mixing until dissolved by hand vortexing. For analyses, 25 µL of the sample were injected into the HPLC system.

EXAMPLE 3

Separation of Isomers Using 1-Hexanol as Mobile Phase Additive

The separation of cis and trans isomers was also tested following the procedure described in Bhat et al., "Effect of 2-alkanols on the separation of geometric isomers of retinol in non-aqueous high-performance liquid chromatography," Journal of Chromatography, 260:129–136 (1983), which describes using 2-alkanols in the mobile phase. Specifically, the isomers of the compound of FIG. 1 was tested by a $C_{18}$ HPLC column using 2-hexanol in the mobile phase.

Figure 6:
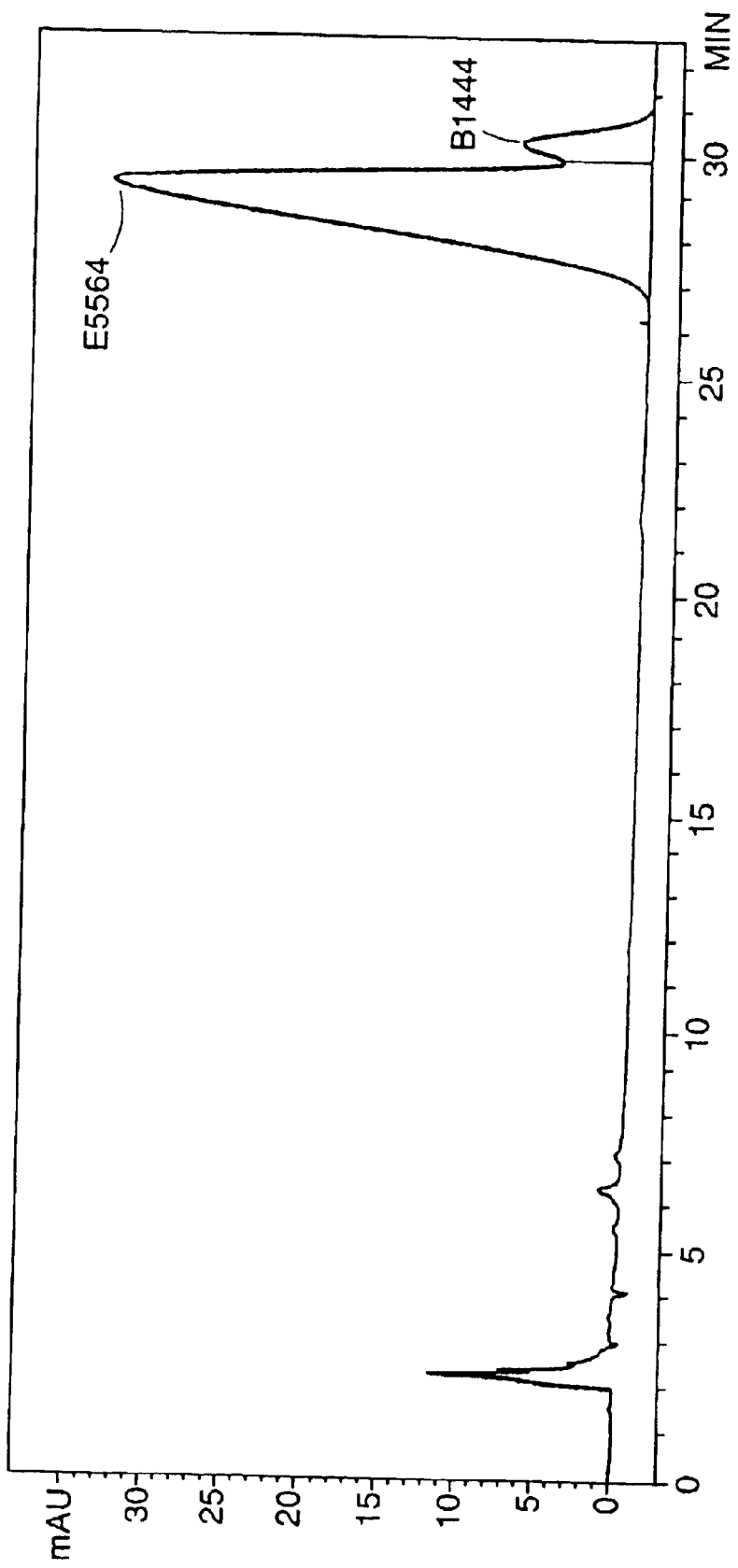
FIG. 6 is a $C_{18}$ HPLC chromatogram of the compound of FIG. 1 and its trans isomer using 1.9% by volume of phosphoric acid, 4.4% by volume of water, 88.9% by volume of methanol and 4.8% by volume of 2-hexanol in the mobile phase.

As shown in FIG. 6, the separation of E5564 from its trans double bond isomer, B1444, was not complete and could only be achieved when the retention time of the mobile phase in the HPLC column was increased to 30 minutes. Unfortunately, such long retention on the HPLC column resulted in unacceptably broad peak shapes.

A $C_{18}$ HPLC column (YMC-Pack ODS-AP 303, 250×4.6 mm, 5 µm particle size, 300 Å pore size; YMC catalog number AA30S05-2546WT) was affixed to a Hewlett Packard 1050 HPLC system and maintained at 20–25° C. The HPLC system was comprised of an autosampler fitted with a 0.1 to 100 µL variable sample loop, a quarternary pump (a solvent delivery system), utilizing low-pressure mixing, and a variable wavelength detector set at 254 nm. The HPLC system was controlled by a computer operating Hewlett Packard ChemStation software version 03.02 for HPLC.

The HPLC column was eluted with phosphoric acid, water, methanol, and 2-hexanol (1.9%, 4.4%, 88.9%, and 4.8% by volume, respectively). HPLC-grade methanol was purchased from J. T. Baker, Phillipsburg, N.J., USA; water was purified by double reverse osmosis then end-polished by a US Filter Modulab™ water purification system; phosphoric acid (85 weight-%, iron content below 1 part per billion)

of biochemical grade was purchased from Wako Chemical, Richmond, Va., USA, and 2-hexanol of 99+% purity was purchased from Aldrich Chemical, Milwaukee, Wis., USA.

A sample was prepared by transferring 5 mg E5564 and 1 mg B1444 (trans double bond isomer of E5564) to an amber HPLC vial, adding 1 mL methanol, capping and mixing until dissolved by hand vortexing. For analyses, 25 μL were injected into the HPLC system.

EXAMPLE 4

Separation of Isomers Using Alkanes and 1-Alkenes

A. Selection of Mobile Phase Additives

In order to determine the effect of various mobile phase additives on separating olefinic isomers, a series of test compounds were investigated using a diverse set of alkanes and 1-alkenes as mobile phase additives. Alkanes and 1-alkenes ranging from 6 to 12 carbon atoms in length were selected for testing as mobile phase additives. Although other alkanes and alkenes (such as those with the unsaturation located at other carbon positions) are within the scope of the invention, the above range was chosen based on the initial results with 1-octene, as given in Example 2, and based on volatility considerations (for example, butane is in the gaseous phase for the temperatures and pressures associated with the process, and thus is unsuitable as a liquid phase additive) and solubility data (dodecane, although successfully solubilized, presented some solubility challenges; tetradecane would likely have presented solubility problems as well). The additives which were tested include hexane, octane, decane, dodecane, 1-hexene, 1-octene, 1-decene, and 1-dodecene. Table 1 lists the names and structures of alkane and 1-alkene mobile phase additives that were tested.

TABLE 1

| Alkane name | alkane structure |
|---|---|
| Hexane | |
| Octane | |
| Decane | |
| Dodecane | |

TABLE 1-continued

| 1-alkene name | 1-alkene structure |
|---|---|
| 1-hexene | |
| 1-octene | |
| 1-decene | |
| 1-dodecene | |

Also, although any number of alkanes and alkenes could have been tested and are within the scope of the invention, considerations of efficiency and commercial availability led to the selection of even carbon number alkanes ($C_6$, $C_8$, $C_{10}$, and $C_{12}$). To test the effect of a 1,2-carbon-carbon double bond, 1-alkenes with corresponding carbon numbers were purchased and utilized.

B. Selection of Olefinic Test Compounds

In addition to testing the effect of the aforementioned mobile phase additives on the E5564 and B1444 separation, the methods of the present invention were applied to other important biomolecules whose separations have been historically difficult. These compounds included retinoids (e.g., retinoic acids, retinals and retinols) and carotenoids (e.g., carotenes). Finally, to complete the scope of the applicability of this work, the alkene chain which is important to the synthesis of E5564, octadecenoic ($C_{18}$) acids in cis- and trans-double bond isomer pairs with the unsaturation located at positions 9, 11, and 13, were examined. The names and structures of the olefinic isomers studied are listed in Table 2, which include E5564 and B1444, octadecenoic acids (C-18 acids) in pairs of (9-, 11-, and 13-cis- and trans-double bond) isomers, retinoic acids, retinals, retinols, and carotene isomers.

TABLE 2

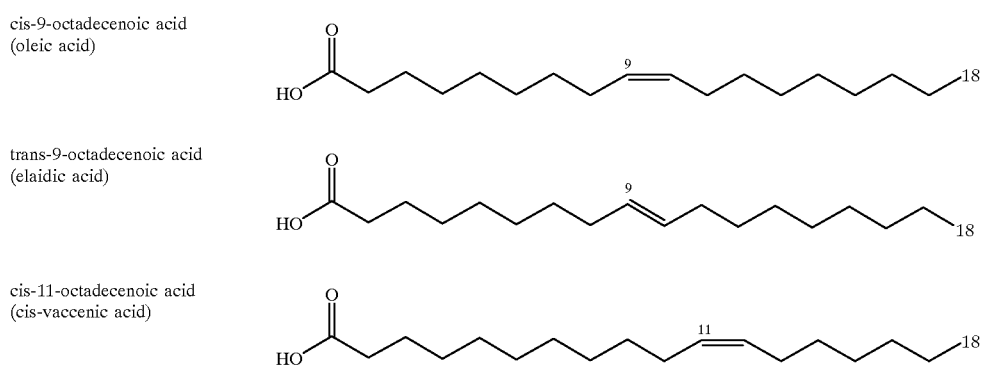

TABLE 2-continued
| | |
|---|---|
| trans-11-octadecenoic acid (trans-vaccenic acid) | 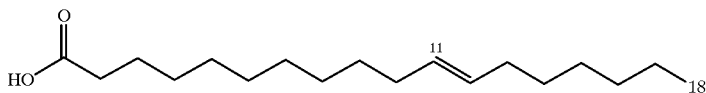 |
| cis-13-octadecenoic acid | 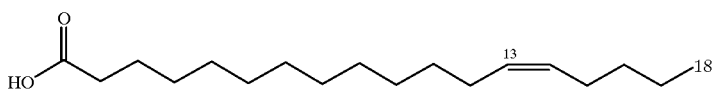 |
| trans-13-octadecenoic acid | 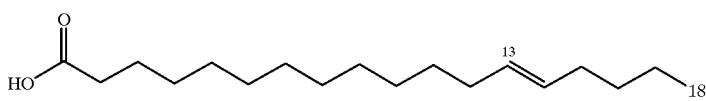 |
| all trans-retinoic acid | 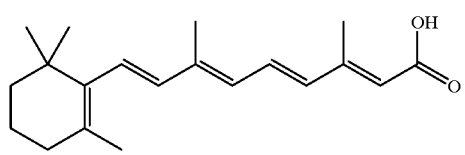 |
| cis-13-retinoic acid | 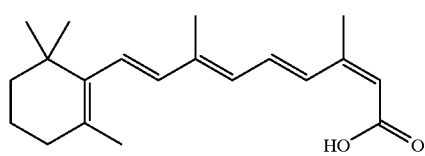 |
| all trans-retinal | 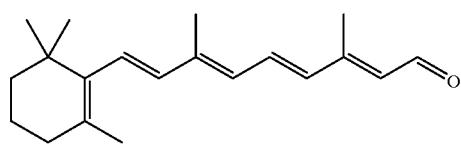 |
| cis-13-retinal | 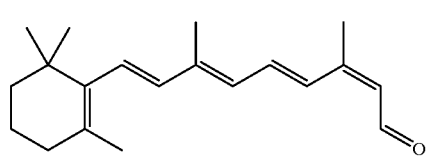 |
| all trans-retinol | 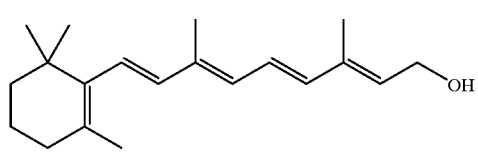 |
| cis-13-retinol | 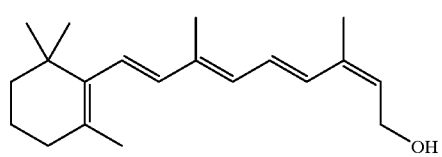 |

TABLE 2-continued
E5564
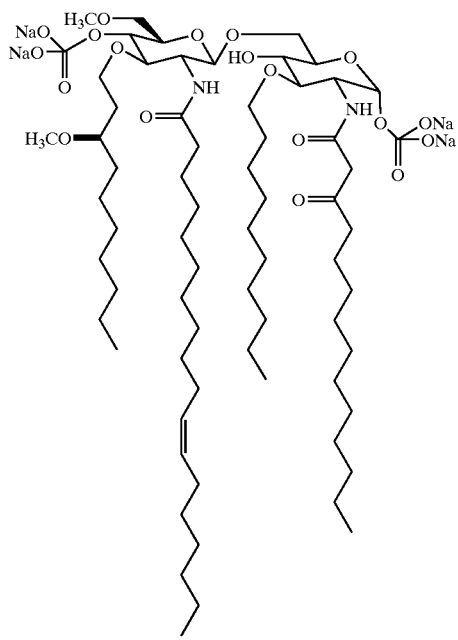
B1444
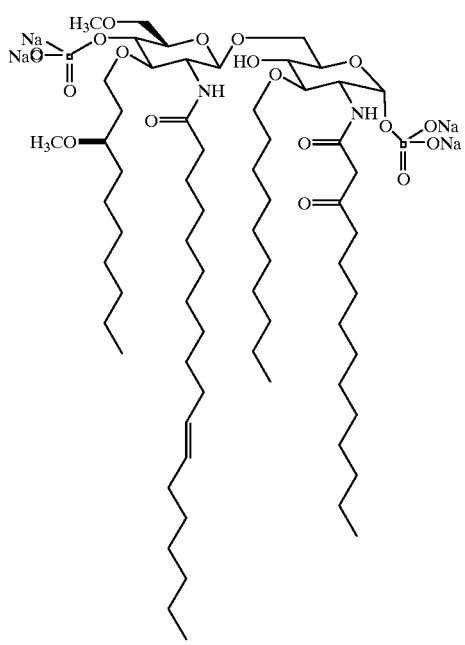
α-carotene, β-carotene, mixed isomers α:β ratio was 1:2 in sample
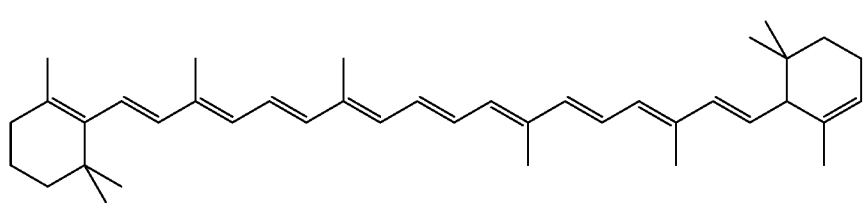
α-carotene TABLE 2-continued

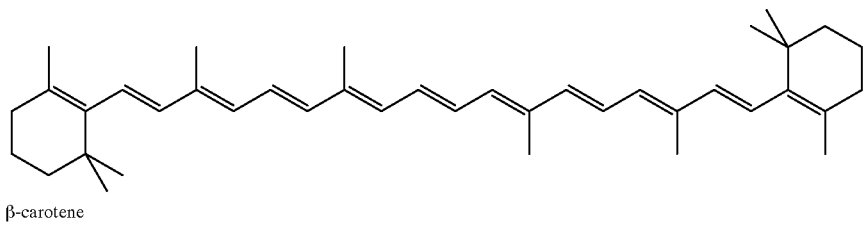

β-carotene

C. Preparation of Mobile Phase Compositions

The mobile phases used for separation were prepared by combining carefully measured quantities of solvents and additives. Table 3 lists the mobile phase composition for each isomeric pair of test compounds.

TABLE 3

| Isomeric Mixtures of Test Compounds (listed according to olefinic isomer pairs) | Mobile phase composition (volumes in mL) | | | |
|---|---|---|---|---|
| | Name of Additive | Additive | $H_3PO_4$ | $H_2O$ | MeOH |

| | Name of Additive | Additive | $H_3PO_4$ | $H_2O$ | MeOH |
|---|---|---|---|---|---|
| cis- and trans-9-octadecenoic acid | none | 0 | 0.15 | 35 | 465 |
| | hexane | 10 | 0.15 | 40 | 450 |
| cis- and trans-11-octadecenoic acid | octane | 10 | 0.15 | 40 | 450 |
| | decane | 10 | 0.15 | 40 | 450 |
| | dodecane | 5 | 0.15 | 40 | 455 |
| cis- and trans-13-octadecenoic acid | 1-hexane | 10 | 0.15 | 40 | 450 |
| | 1-octene | 10 | 0.15 | 40 | 450 |
| | 1-decene | 10 | 0.15 | 40 | 450 |
| cis- and trans-13-retinoic acid cis- and trans-13-retinal cis- and trans-13-retinol | 1-dodecene | 5 | 0.15 | 40 | 455 |
| α- and β-carotenes | none | 0 | 0.15 | 0 | 500 |
| | hexane | 10 | 0.15 | 5 | 485 |
| | octane | 10 | 0.15 | 6 | 484 |
| | decane | 10 | 0.15 | 6 | 484 |
| | dodecane | 5 | 0.15 | 5 | 490 |
| | 1-hexane | 10 | 0.15 | 6 | 484 |
| | 1-octene | 10 | 0.15 | 6 | 484 |
| | 1-decene | 10 | 0.15 | 6 | 484 |
| | 1-dodecene | 5 | 0.15 | 5 | 490 |
| E5564 and B1444 | none | 0 | 10 | 11 | 479 |
| | hexane | 10 | 10 | 15 | 465 |
| | octane | 10 | 10 | 17 | 463 |
| | decane | 10 | 10 | 17 | 463 |
| | dodecane | 7 | 10 | 17 | 466 |
| | 1-hexane | 10 | 10 | 16 | 464 |
| | 1-octene | 10 | 10 | 17 | 463 |
| | 1-decene | 10 | 10 | 17 | 463 |
| | 1-dodecene | 7 | 10 | 17 | 466 |

Mobile phase additives (hexane, octane, decane, dodecane, 1-hexene, 1-decene, and 1-dodecene) were obtained from Aldrich (Milwaukee, Wis.), 1-octene was purchased from Acro Organics (NJ, USA), reagent grade phosphoric acid was obtained from Aldrich (Milwaukee, Wis.). Methanol and n-heptane (HPLC grade) were purchased from J. T. Baker (Phillipsburg, N.J.), HPLC grade water was obtained from a US Filter Modulab™ water system (United States Filter Corporation), E5564 was synthesized by Eisai Research Institute, and B1444 was provided by Eisai Company, Ltd., Japan. All cis- and trans-isomers of octadecenoic acids, carotenes, retinoic acids, retinals, and retinols were purchased from Sigma (St. Louis, Mo.).

Each test compound (except for the carotenes) was prepared as a diluted solution in methanol and combined in the same HPLC vials as pairs of cis- and trans-isomers. The concentrations of E5564 and B1444 were 5 and 1 mg/mL, respectively. The concentrations of octadecenoic acids in pairs of cis- and trans-isomers were approximately 6 mg/mL each. Retinoic acids, retinals, and retinols in pairs of cis- and trans-isomers were approximately 1 mg/mL each. Carotene in mixed isomers was dissolved in n-heptane at a concentration of approximately 1 mg/mL, total, and the ratio of α- and β-isomers was approximately 1 to 2, respectively.

The mobile phase consisted of 0.03% phosphoric acid (except for E5564 and B1444 separations, which was 2% phosphoric acid), water, methanol and 2% of mobile phase additive (except for dodecane and 1-dodecene, which were at lower concentrations of 1.0 and 1.4%, respectively, due to their reduced solubilities).

The tests were conducted using a Hewlett-Packard HP1100 liquid chromatography system (Waldbronn, Germany) equipped with a ternary pump, low pressure mixing, a variable wavelength detector, a temperature controlled column compartment, a variable loop auto-injector, 0.1 to 100 μL range and a vacuum degasser. Data analysis was performed on HP ChemStation for HPLC software version 03.02. The separation was performed on a YMC-PACK ODS-AP303, 5 μm, 300 Å, 250×4.6 mm column (Waters Corporation, Milford, Mass.).

The flow rate of the mobile phase was 1.0 mL/min. The column temperature was 30° C. (except for E5564 and B1444 experiments, in which the column temperature was 35° C.). The detector was set at 210 nm. The injection volume was 10 μL. Carotene solution was injected five times for system precision and reproducibility. All other test compounds were injected once. Sample diluents methanol and n-heptane were used as injection blanks, as appropriate, as control experiments for sample injections.

Scouting experiments were performed on the HPLC with various mobile phases in order to determine the correct methanol and water ratios that would allow the series of test compounds to elute at about the same retention time (with the same k' value, where $k'=(t_r-t_0)/t_0$, where $t_r$=retention time of the peak of interest, and $t_0$=retention time of an unretained peak). A control experiment with no additive added was performed for each set of test compounds.

D. Experimental Reproducibility Tests

The reproducibility of the results obtained by the method was examined. One test compound solution (carotenes) was analyzed five times. The resolution, retention times, and peak areas of the test compounds were recorded each time.

As used herein, the term "resolution" is defined by the equation: resolution=$2(t_2-t_1)/(w_1+w_2)$, where $t_1$ and $t_2$ are defined as the retention times of the earlier and later eluting peaks, respectively, and $w_1$ and $w_2$ are the peak widths of the earlier and later eluting peaks, respectively, determined by extrapolating the flat portions of the peak sides down to the baseline. The relative standard deviations of the resolution, retention time, and peak area responses are listed in Table 4.

TABLE 4

| Additive | Resolution | % RSD* | ret. time | % RSD* | area count | % RSD* |
|---|---|---|---|---|---|---|
| octane | 1.23 | 0.72 | 19.02 | 0.05 | 1758.9 | 0.25 |
| decane | 1.26 | 0.36 | 19.04 | 0.07 | 1743.9 | 0.80 |
| 1-decene | 1.27 | 0.43 | 19.62 | 0.04 | 1600.1 | 0.57 |
| 1-dodecene | 1.33 | 0.34 | 20.29 | 0.06 | 1473.8 | 0.33 |

*n = 5

The relative standard deviations (RSD) of all three parameters were less than 1.0%. This demonstrated the reproducibility of the HPLC analysis. After conducting performance validation of the HPLC equipment, and confirming proper calibration, a single batch of mobile phase was used for each compound in the octadecenoic acid, retinoic acid, retinal, and retinal series as shown in Table 3. For example, one batch of hexane-containing mobile phase was prepared and used for the analysis of the 9-, 11-, and 13-octadecenoic acids, retinoic acids, retinals, and retinols. Due to polarity differences, three separate hexane containing mobile phases were used for the E5564 and carotene analyses.

E. Effect of Mobile Phase Additives on Olefinic Isomer Pair Separations

The principle of the separation using mobile phase additives described herein, namely, the alkanes, hexane, octane, decane, and dodecane, and the 1-alkenes, 1-hexene, 1-octene, 1-decene, and 1-dodecene is not yet clearly understood. However, it was observed for the series of compounds tested, that the presence of a carboxylic acid or a phosphate group (which contains both ionic and polar groups) correlated with the alkane and 1-alkene mobile phase additives having a positive effect on the chromatographic separation of the cis- and trans-carbon-carbon double bond isomers. The addition of alkane and 1-alkene substances to HPLC mobile phases appears to be an effective way to enhance the selectivity of the HPLC separation of acid olefinic isomers. Substances not containing acidic functional groups were not responsive to the positive separation effects of these alkanes and 1-alkenes.

As shown below, the use of alkane and 1-alkene as a mobile phase additive in HPLC is an effective way to alter selectivity and retention mechanisms for separation of certain types of olefinic isomers bearing acidic functional groups. The method of the present invention was useful for separating E5564 and B1444, octadecenoic cids described herein, and retinoic acids described herein. However, this technique was not as successful in the separations of the non-acidic retinals, retinols, and carotenes described herein. Increasing chain length on the series of mobile phase alkane and 1-alkene additives had a positive effect on the separation. These results indicate that if solubility issues are resolved, longer alkene and alkane chains may be employed in this separation process. On the other hand, the use of a 1-alkene did not provide any advantage over using an alkane in conclusion, this technique provides a useful and complementary method to HPLC for the separation of these types of compounds that can be difficult to separate by conventional HPLC techniques.

1. Retention Time and Resolution

Table 5 lists the retention times of all cis-double bond test compounds for each mobile phase additive that was tested.

TABLE 5

| | Retention Time (in seconds) Mobile Phase Additive | | | | | | | | |
|---|---|---|---|---|---|---|---|---|---|
| Test Compound | control | hexane | octane | decane | dodecane | 1-hexene | 1-octene | 1-decene | 1-dodecene |
| cis-9-octadecenoic acid | 6.4 | 6.5 | 6.7 | 6.5 | 6.8 | 6.6 | 6.5 | 6.7 | 7.0 |
| cis-11-octadecenoic acid | 6.5 | 6.5 | 6.6 | 6.5 | 6.8 | 6.6 | 6.5 | 6.7 | 6.9 |
| cis-13-octadecenoic acid | 6.6 | 6.6 | 6.7 | 6.6 | 6.9 | 6.7 | 6.6 | 6.8 | 7.0 |
| cis-13-retinoic acid | 5.2 | 5.1 | 5.1 | 4.9 | 5.1 | 5.2 | 5.2 | 5.1 | 5.3 |
| cis-13-retinal | 5.6 | 5.6 | 5.6 | 5.5 | 5.7 | 5.7 | 5.7 | 5.7 | 5.8 |
| cis-13-retinol | 5.4 | 5.3 | 5.3 | 5.2 | 5.3 | 5.4 | 5.4 | 5.3 | 5.5 |
| E5564 | 18.7 | 18.4 | 17.1 | 16.5 | 18.0 | 16.9 | 16.8 | 16.2 | 17.3 |
| carotene, α isomer | 19.1 | 18.4 | 19.0 | 19.0 | 20.3 | 19.8 | 19.4 | 19.6 | 20.3 |

It is generally known to one of skill in the art that increased retention times result in higher resolution. An effort was made, when testing pairs of cis- and trans-double bond isomers, to keep their respective retention times constant regardless of the mobile phase additive used, so that the isomer resolution results could be compared for a series of mobile phase additives. For example, an effort was made to ensure that the retention time of cis-9-octadecenoic acid was approximately the same when chromatographed with or without the presence of a mobile phase additive.

The retention time was observed to vary from 6.4 to 7.0 minutes. Thus, the difference in the resolution of various cis-and trans-double bond isomers, as shown in Table 6, may be attributed to the effect of the mobile phase additive rather than the retention time.

TABLE 6

| Isomeric Mixtures of Test Compounds | Resolution Mobile Phase Additive | | | | | | | |
|---|---|---|---|---|---|---|---|---|
| | control | hexane | octane | decane | dodecane | 1-hexene | 1-octene | 1-decene | 1-dodecene |
| cis- and trans-9-octadecenoic acids | 0.46 | 0.59 | 0.75 | 0.70 | 0.93 | 0.67 | 0.68 | 0.78 | 0.78 |
| cis- and trans-11-octadecenoic acids | N/O | 0.47 | 0.67 | 0.72 | 0.84 | 0.46 | 0.50 | 0.69 | 0.70 |
| cis- and trans-13-octadecenoic acids | N/O | 0.44 | 0.60 | 0.70 | 0.71 | 0.40 | 0.42 | 0.63 | 0.69 |
| Cis- and trans-13-retinoic acids | 1.28 | 1.39 | 1.54 | 1.52 | 1.71 | 1.37 | 1.41 | 1.60 | 1.70 |
| cis- and trans-13-retinals | N/O | N/O | N/O | N/O | N/O | N/O | N/O | N/O | N/O |
| cis- and trans-13-retinols | N/O | N/O | N/O | N/O | N/O | N/O | N/O | N/O | N/O |
| E5564 and B1444 | 0.83 | 1.02 | 1.04 | 1.08 | 1.22 | 1.00 | 1.03 | 1.05 | 1.08 |
| α- and β-carotene | 1.29 | 1.23 | 1.24 | 1.26 | 1.32 | 1.25 | 1.25 | 1.27 | 1.34 |

N/O = separation was not observed

Table 5 shows that the retention times of each cis-double-bond isomer was kept nearly constant (within 5% relative standard deviation) for a series of mobile phase alkane and 1-alkene additives tested. Under control conditions, where no mobile phase alkane or alkene additive were present, little to no resolution of double-bond isomeric pairs was achieved by HPLC using the C-18 column. In general, the addition of mobile phase additives had an improved effect on the isomeric pair resolution. This was the case for E5564 and B1444, cis- and trans-9-, 11-, and 13-octadecenoic acids, and cis- and trans-retinoic acids. However, the addition of alkane or 1-alkene additives to the mobile phase had little to no effect on the retinal, retinol, and carotene separations.

2. Separation of E5564 and B1444

Figure 7:
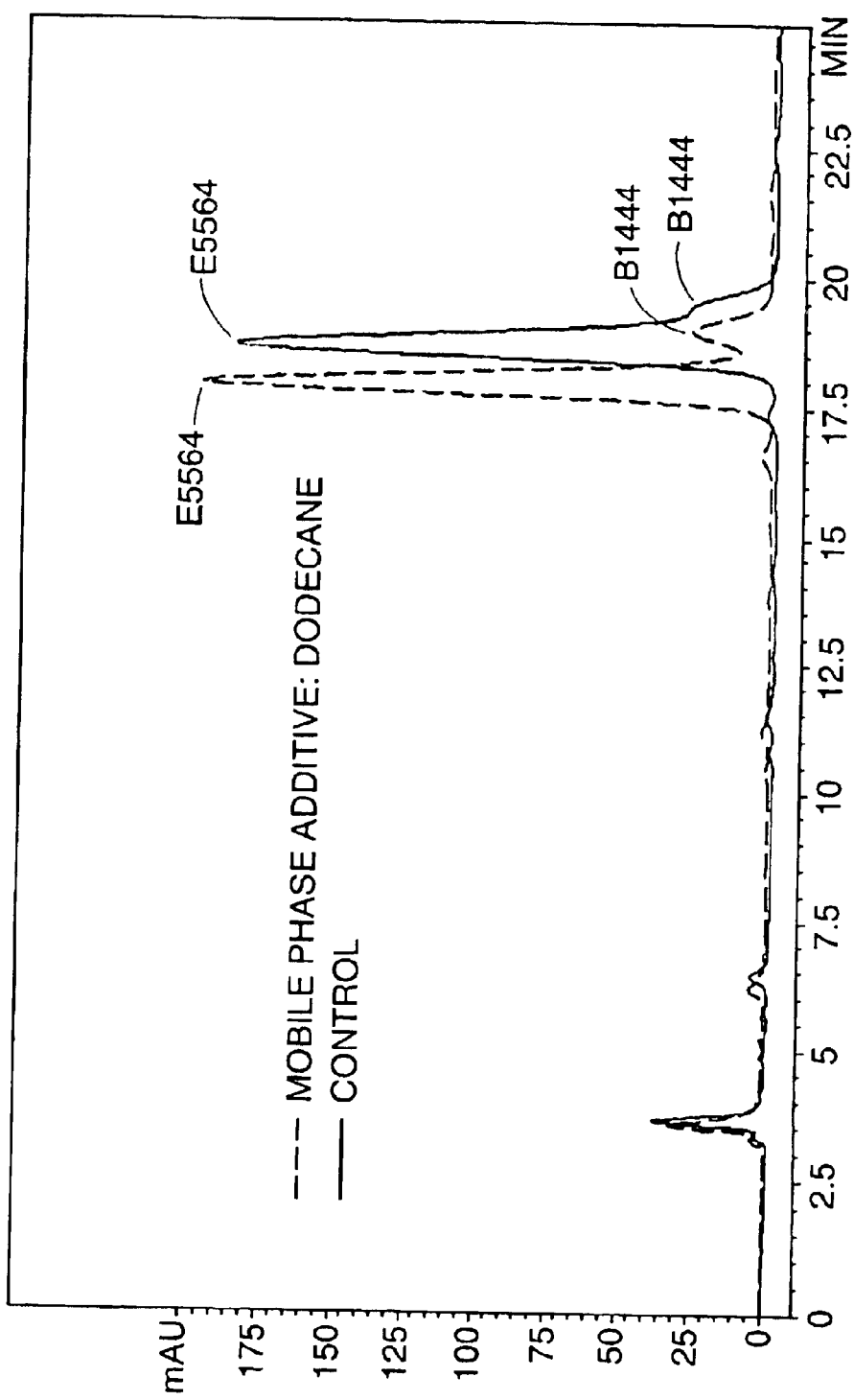
FIG. 7 is a graphical representation of two overlapped chromatograms showing improved separation of E5564 and B1444 isomers in the presence of the mobile phase additive, dodecane, than without the additive.

In the separation of E5564 (cis-) and B1444 (trans-) isomers, 1-alkenes facilitated no better resolution than the corresponding alkanes. However, it was found that longer chain length alkanes and 1-alkenes provided better resolution than their shorter chain length homologues. For example, dodecane facilitated a 1.22 resolution of E5564 and B1444 while hexane only promoted a resolution of 1.02. In other words, the separation quality increased with increasing chain length. A similar trend was observed when 1-alkenes were used as mobile phase additives. FIG. 7 is a graphical representation of two overlapped chromatograms showing improved separation of E5564 and B1444 isomers in the presence of the mobile phase additive, dodecane, than without the additive.

3. Separation of Cis- and Trans-Octadecenoic Acid

In all of the tests conducted, the alkane or 1-alkene additive had a positive effect on the separation of the olefinic isomer pairs of cis- and trans-octadecenoic acids (unsaturated at $C_9$–$C_{10}$, $C_{11}$–$C_{12}$, and $C_{13}$–$C_{14}$. Similar to E5564 and B1444, increasing alkane chain length improved the isomeric pair resolution in the order of: hexane<octane<decane<dodecane. The same was observed with the 1-alkenes: the separation quality improved in the series as follows: 1-hexene<1-octene<1-decene<1-dodecene. For example, no separation was observed between cis- and trans-11-octadecenoic acids without a mobile phase additive.

Figure 8:
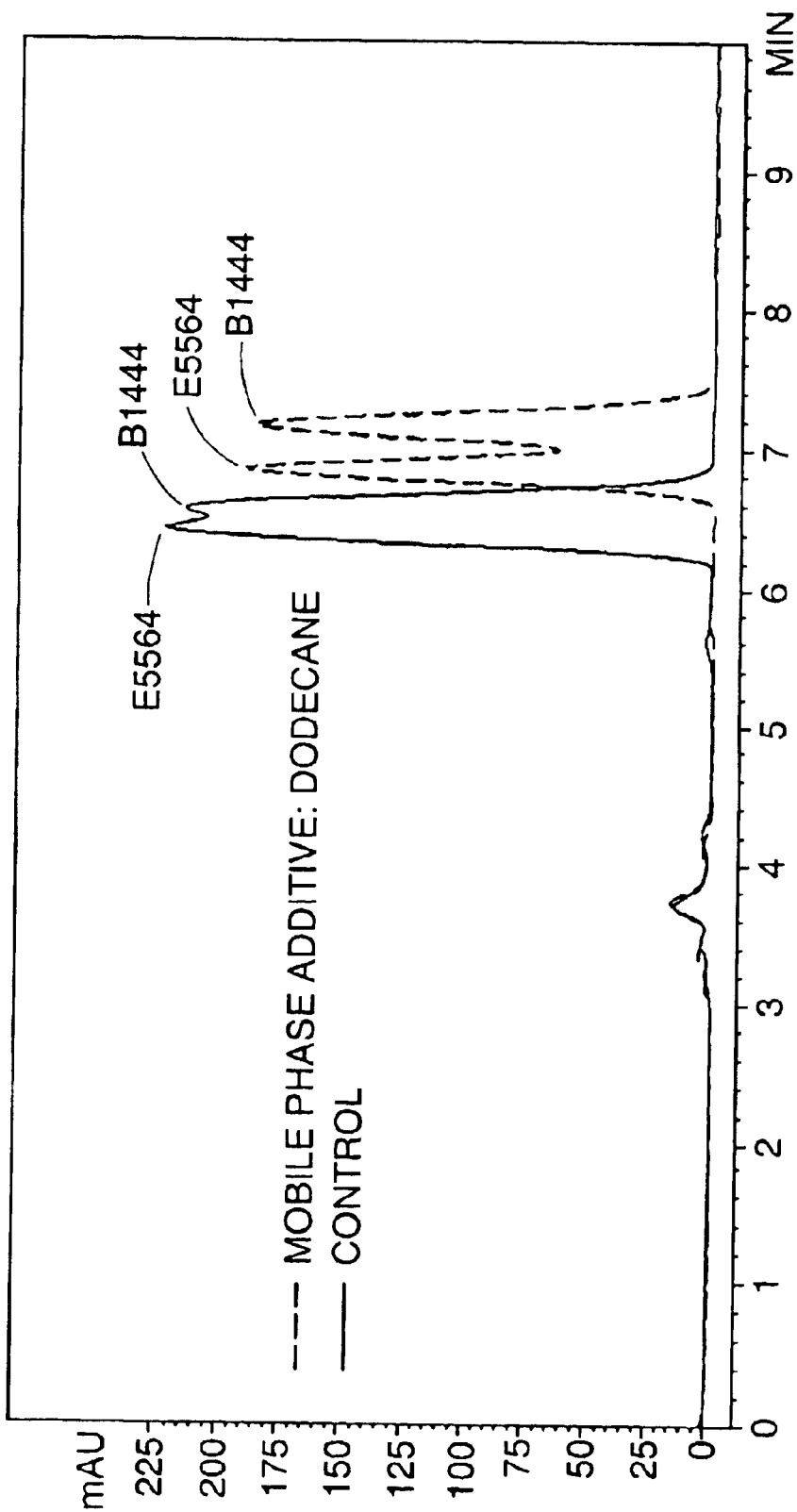
FIG. 8 is a graphical representation of two overlapped chromatograms showing improved separation of cis- and trans-9-octadecenoic acid isomers in the presence of the mobile phase additive, dodecane, than without the additive.
Figure 9:
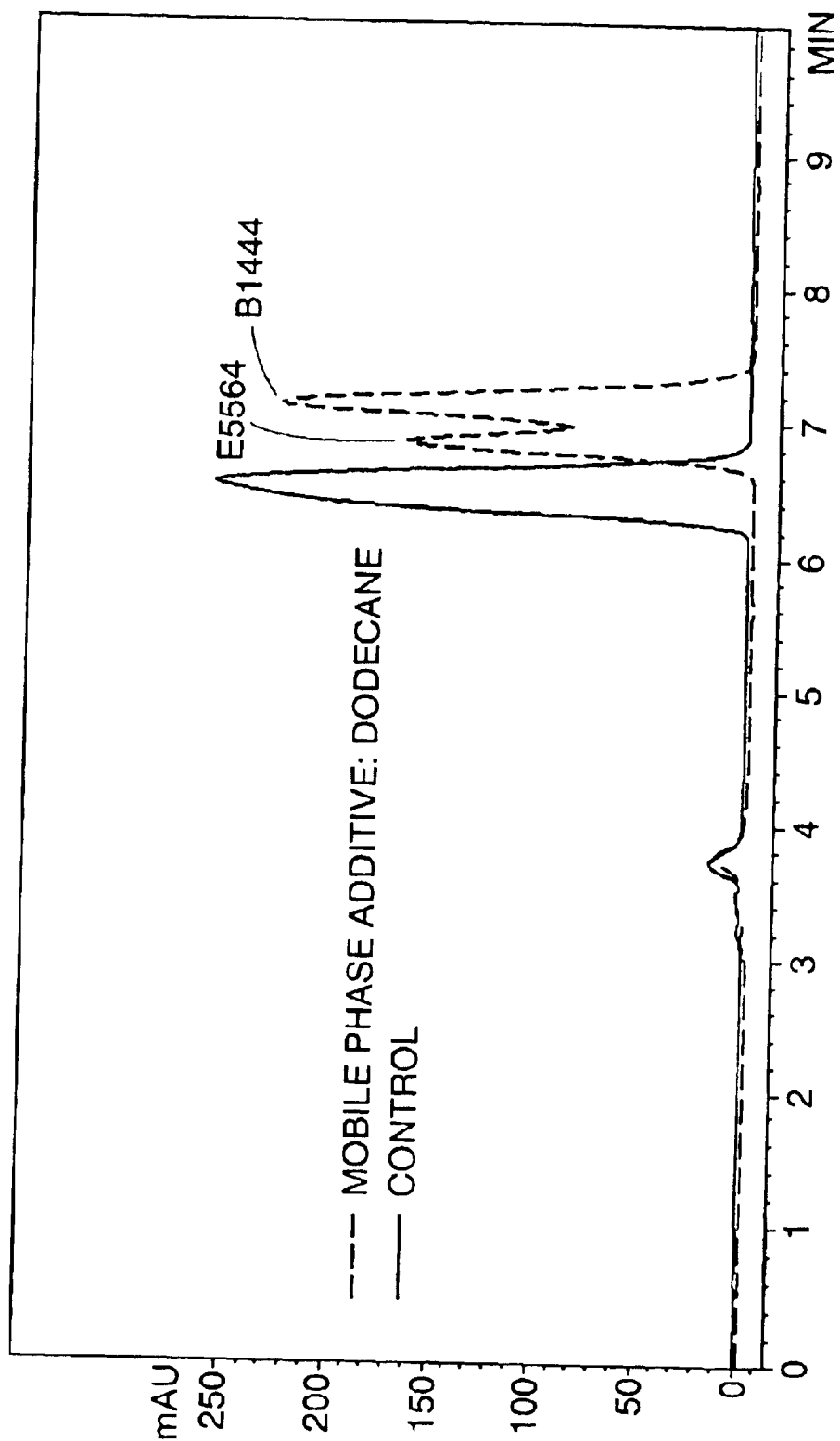
FIG. 9 is a graphical representation of two overlapped chromatograms showing improved separation of cis- and trans-11-octadecenoic acid isomers in the presence of the mobile phase additive, dodecane, than without the additive.
Figure 10:
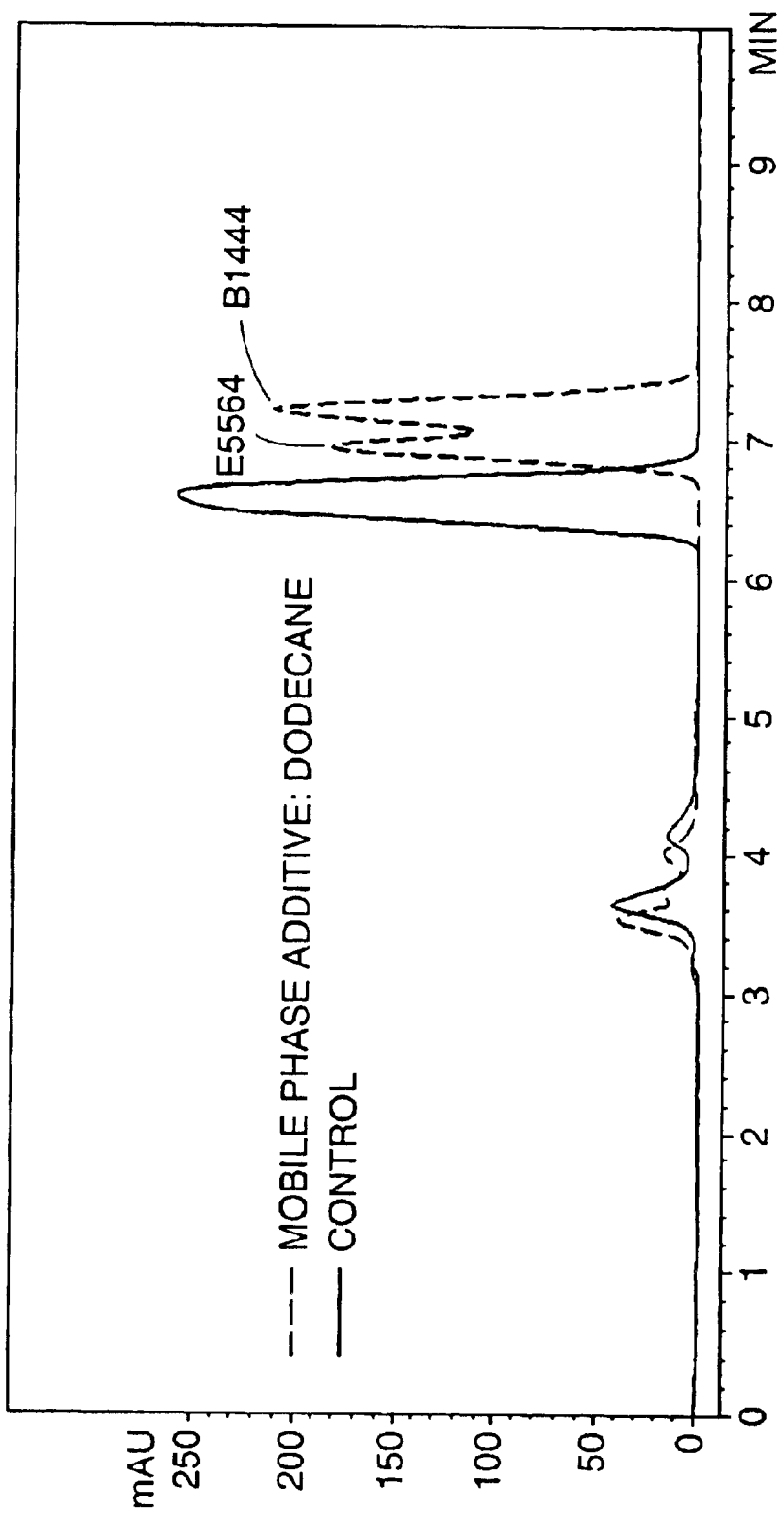
FIG. 10 is a graphical representation of two overlapped chromatograms showing improved separation of cis- and trans-13-octadecenoic acid isomers in the presence of the mobile phase additive, dodecane, than without the additive.

However, the resolution improved to 0.47 and 0.46 with the additions of hexane and 1-hexene, respectively, and the best separations were observed with dodecane and 1-dodecene, where the resolutions were 0.84 and 0.70, respectively. FIG. 8 shows marked improvement in the separation of cis and trans-9-octadecenoic acid when dodecane was added as the mobile phase additive. This trend was observed as well in cis- and trans-9- and 13-octadecenoic acids with the addition of hexane and 1-hexene. Similar results, as shown in FIGS. 9 and 10, were observed for 11- and 13-octadecenoic acids, respectively. Compared to control chromatograms, improved separation was observed with the addition of dodecane as a mobile phase additive.

4. Separation of Cis- and Trans- Retinoic Acid

Figure 11:
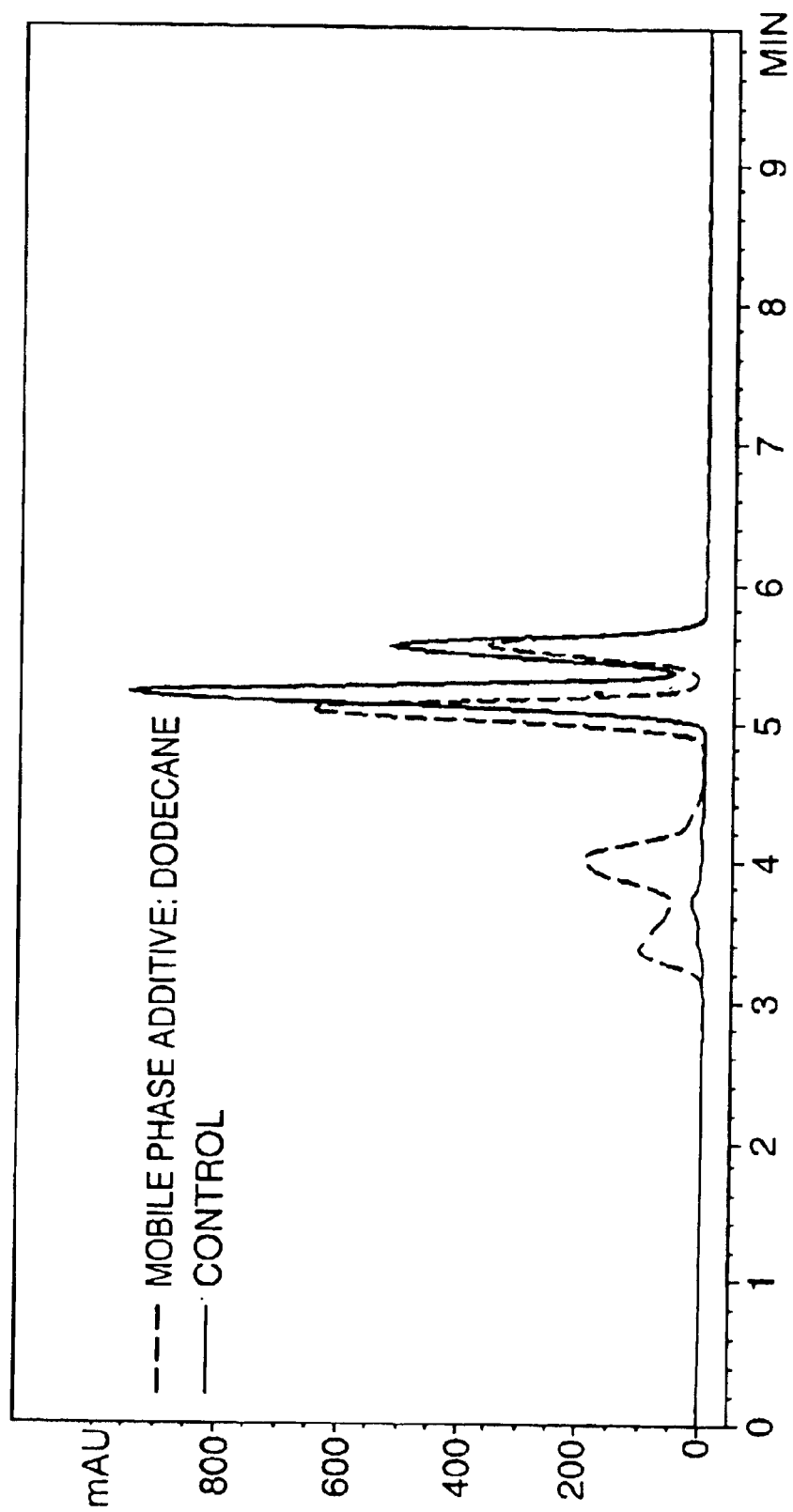
FIG. 11 is a graphical representation of two overlapped chromatograms showing improved separation of cis and trans-13-retinoic acid when dodecane was added as the mobile phase additive.

A resolution of 1.28 was observed for cis- and trans-13-retinoic acid to which neither an alkane nor 1-alkene had been added as a mobile phase additive. As was observed with E55664 and its double bond isomer, B1444, and the cis- and trans-octadecenoic acids, the addition of an alkane or 1-alkene improved the resolution. For example, the resolution improved to 1.39 and 1.37 when hexane and 1-hexene were added, respectively. Again, the resolution effected by an alkane or 1-alkene additive increased with additive chain length. For example, the resolution quality for cis- and trans-13-retinoic acids followed the pattern of mobile phase additive use as follows: hexane<octane<decane<dodecane and 1-hexene<1-octene<1-decene<1-dodecene. FIG. 11 shows marked improvement in the separation of cis and trans-13-retinoic acid when dodecane was added as the mobile phase additive.

5. Separation of Retinals, Retinols, and Carotenoids

Meaningful separation of the retinal and retinal isomeric pairs was not observed either in the presence or in the absence of an alkane or 1-alkene mobile phase additive. Interestingly, these compounds are not carboxylic acids. Also, the retinoic acid, retinal, and retinol retention times were all in the range of 4.9 to 5.8 minutes, with a flow rate of 1.0 mL/min, indicating that the lack of separation was not due to too short a retention time or the HPLC column.

Finally, while the carotenes were among the best separated compounds under the control conditions, no significant improvement in the carotene isomer separation upon the addition of any alkane or 1-alkene mobile phase additive was observed. For example, the resolution observed without an additive was 1.29, while the use of hexane, 1-hexene, octane, 1-octene, decane, 1-decene, dodecane, and 1-dodecene resulted in resolution values of 1.23, 1.25, 1.24, 1.25, 1.26, 1.27, 1.32, and 1.34, respectively. These values do not represent significant improvements over the resolution afforded in the absence of alkane and 1-alkene mobile phase additives.

The various technical and scientific terms used herein have meanings that are commonly understood by one of ordinary skill in the art to which the present invention pertains. As is apparent from the foregoing, a wide range of suitable materials and/or methods known to those of skill can be utilized in carrying out the present invention; however, preferred materials and/or methods have been described. Materials, substrates, and the like to which reference is made in the foregoing description and examples are obtainable from commercial sources, unless otherwise noted. Further, although the foregoing invention has been described in detail by way of illustration and example for purposes of clarity and understanding, these illustrations are merely illustrative and not limiting of the scope of the invention. Other embodiments, changes and modifications, including those obvious to persons skilled in the art, will be within the scope of the following claims.

What is claimed is:

1. A process for separating cis and trans isomers in a mixture of geometric isomers of an olefinic compound, the process comprising:

(a) flowing a mobile phase through a column means containing a stationary phase comprising an organosilane having a pendant aliphatic functional group attached to a solid support, the mobile phase comprising an aliphatic hydrocarbon and a mixture of cis and trans isomers of a compound of the formula:

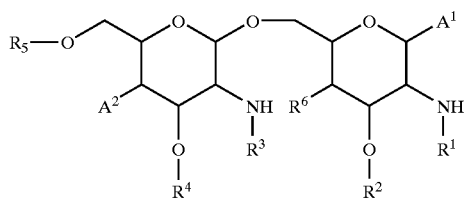

where $R^1$ is selected from the group consisting of

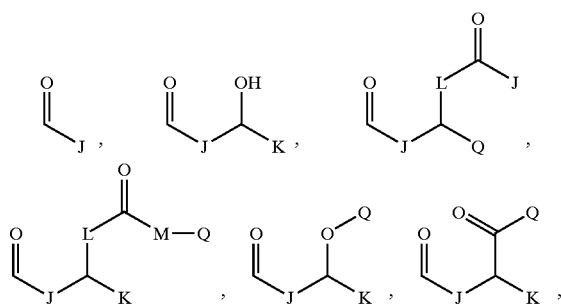

-continued

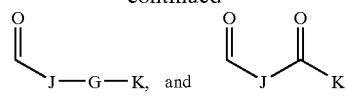

where each J, K and Q, independently, is straight or branched C1 to C15 alkyl; L is O, NH or $CH_2$; M is O or NH; and G is NH, O, S, SO, or $SO_2$;

$R^2$ is straight or branched C5 to C15 alkyl;

$R^3$ is selected from the group consisting of

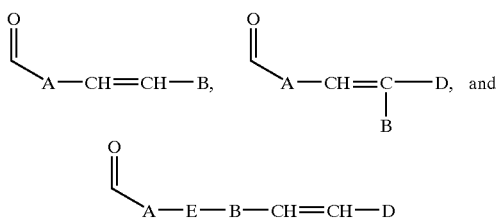

where E is N, O, S, SO, or $SO_2$; each A, B and D, independently, is straight or branched C1 to C15 alkyl;

$R^4$ is selected from the group consisting of straight or branched C4 to C20 alkyl, and

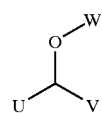

where each U and V, independently, is straight or branched C2 to C15 alkyl and W is hydrogen or straight or branched C1 to C5 alkyl;

$R^5$ is selected from the group consisting of hydrogen, J',-J'-OH,-J'-O—K',-J -O—K'-OH, and -J'-O—PO $(OH)_2$, where each J' and K', independently, is straight or branched C1 to C5 alkyl;

$R^6$ is selected from the group consisting of hydroxy, halogen C1 to C5 alkoxy and C1 to C5 acyloxy;

$A^1$ and $A^2$, independently, are selected from the group consisting of

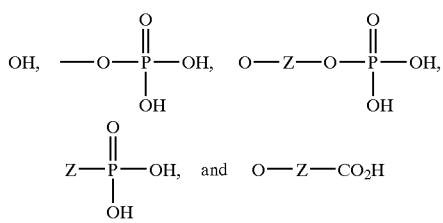

where Z is straight or branched C1 to C10 alkyl; or pharmaceutically acceptable salts thereof, wherein constituents of the mobile phase preferentially interact with the stationary phase and produce an eluent stream, a first portion of which is substantially comprised of the cis isomer and a second portion of the eluent stream which is substantially comprised of the trans isomer;

(b) collecting a first portion of the eluent stream substantially comprising the cis isomer; and (c) collecting a second portion of the effluent stream, substantially comprising the trans isomer.

2. The process of claim 1, wherein the aliphatic hydrocarbon in the mobile phase comprises alkanes or alkenes having the formula $C_nH_{2n+2}$ or $C_nH_{2n}$, respectively, where n=4 to n=16.

3. The process of claim 2, wherein n=6 to n=12.

4. The process of claim 1, wherein the acidic functional group is a carboxyl or a phosphate group.

5. The process of claim 1, wherein the aliphatic hydrocarbon comprises hexane, octane, decane, dodecane, 1-hexene, 1-octene, 1-decene, or 1-dodecene.

6. The process of claim 1, wherein the mobile phase comprises phosphoric acid, water, methanol, and an aliphatic carbon comprising an alkane or 1-alkene having the formula $C_nH_{2n+2}$ or $C_nH_{2n}$, respectively, where n=4 to n=16.

7. The process of claim 1, wherein the column means comprises a $C_{18}$ or $C_{30}$ column.

8. The process of claim 1, wherein the olefinic compound is selected from the group consisting of liposaccharides, alkenoic acids, and retinoic acids.

9. A process for separating cis and trans isomers in a mixture of geometric isomers of a liposaccharide of formula (I):

the process comprising:
(a) flowing a mobile phase through a column means containing a stationary phase comprising an organosilane having a pendant aliphatic functional group attached to a solid support,
the mobile phase comprising (i) a mixture of cis and trans isomers of the liposaccharide of formula I and (ii) an aliphatic hydrocarbons, wherein constituents of the mobile phase preferentially interact with the stationary phase and produce an eluent stream, a first portion of which is substantially comprised of the cis isomer and a second portion of the eluent stream which is substantially comprised of the trans isomer.
(b) collecting a first portion of the eluent stream substantially comprising the cis isomer; and
(c) collecting a second portion of the effluent stream, substantially comprising the trans isomer.

10. The process of claim 9, wherein the aliphatic hydrocarbon in the mobile phase comprises alkanes or alkenes having the formula $C_nH_{2n+2}$ or $C_nH_{2n}$, respectively, where n=4 to n=16.

11. The process of claim 9, wherein n=6 to n=12.

12. The process of claim 9, wherein the aliphatic hydrocarbon comprises hexane, octane, decane, dodecane, 1-hexene, 1-octene, 1-decene, or 1-dodecene.

13. The process of claim 9, wherein the mobile phase comprises phosphoric acid, water, methanol, and an aliphatic carbon comprising an alkane or 1-alkene having the formula $C_nH_{2n+2}$ or $C_nH_{2n}$, respectively, where n=4 to n=16.

14. The process of claim 9, wherein the column means comprises a $C_{18}$ or $C_{30}$ column.

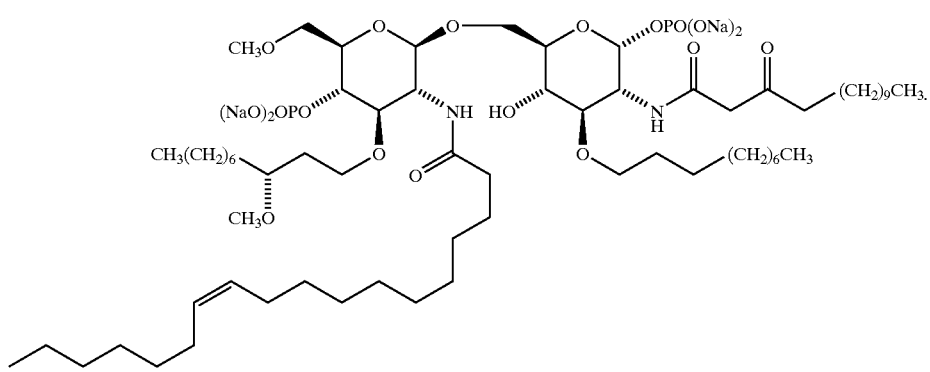

15. The process of claim 6, wherein the aliphatic hydrocarbon comprises hexane, octane, decane, dodecane, 1-hexene, 1-octene, 1-decene, or 1-dodecene.

16. A process for increasing the resolution of cis and trans isomer in a mixture of geometric isomers of a liposaccharide of formula (I):

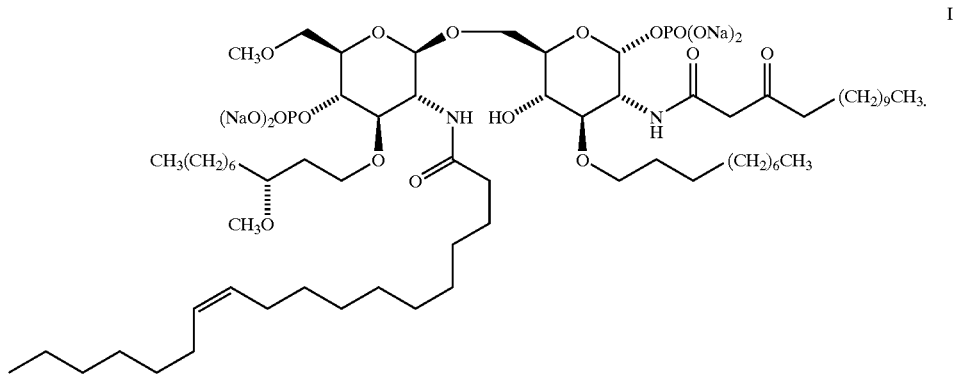

the process comprising:
(a) flowing a mobile phase through a column means containing stationary phase comprising an organosilane having a pendant aliphatic functional group attached to a solid support,
the mobile phase comprising (i) a mixture of cis and trans isomers of the liposaccharide of formula I and (ii) a compound selected from the group consisting of hexane, octane, decane, dodecane, 1-hexene, 1-octene, 1-decene, or 1-dodecene,
wherein constituents of the mobile phase preferentially interact with the stationary phase and produce an eluent stream, a first portion of which is substantially comprised of the cis isomer and a second portion of the eluent stream which is substantially comprised of the trans isomer.
(b) collecting a first portion of the eluent stream substantially comprising the cis isomer; and
(c) collecting a second portion of the effluent stream, substantially comprising the trans isomer.

17. The process of claim 16, wherein the column means comprises a $C_{18}$ or $C_{30}$ column.

18. A process for separating cis and trans isomers in a mixture geometric isomers of an octadecenoic acid or retinoic acid, the process comprising:
(a) flowing a mobile phase through a column means containing a stationary phase comprising an organosilane having a pendant aliphatic functional group,
the mobile phase comprising (i) a compound selected from the group consisting of hexane, octane, decane, dodecane, 1-hexene, 1-octene 1-decene, and 1-dodecene, (ii) attached to a solid support mixture of cis and trans isomers of a compound of the formula:

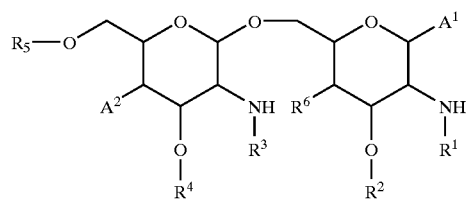

where $R^1$ is selected from the group consisting of

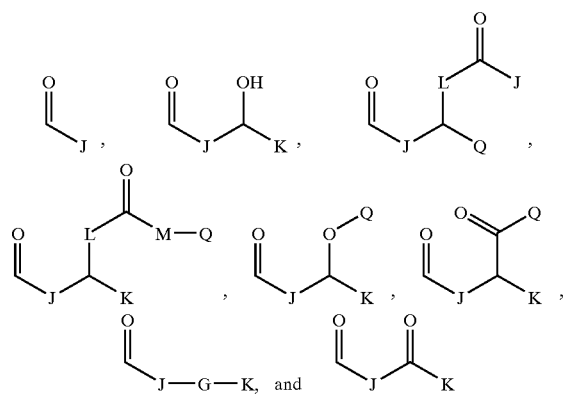

where each J, K and Q, independently, is straight or branched C1 to 15 alkyl; L is O, NH or $CH_2$; M is O or NH; and G is NH, O, S, SO, or $SO_2$;

$R^2$ is straight or branched C5 to C15 alkyl;
$R^3$ is selected from the group consisting of

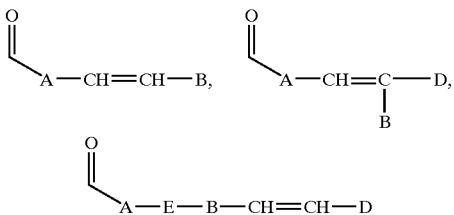

where E is N, O, S, SO, or $SO_2$; each A, B and D, independently, is straight or branched C1 to C15 alkyl;
$R^4$ is selected from the group consisting of straight or branched C4 to C20 alkyl, and

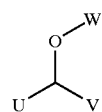

where each U and V, independently, is straight or branched C2 to C15 alkyl and W is hydrogen or straight or branched C1 to C5 alkyl;
$R^5$ is selected from the group consisting of hydrogen, J',-J'-OH, -J'-O—K',-J '-O—K'—OH, and -J'-O—PO$(OH)_2$, where each J' and K', independently, straight or branched C1 to C5 alkyl;
$R^6$ is selected from the group consisting of hydroxy, halogen, C1 to C5 alkoxy and C1 to C5 acyloxy;
$A^1$ and $A^2$, independently, are selected from the group consisting of

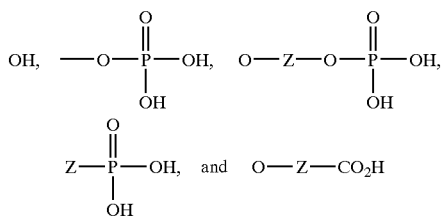

where Z is straight or branched C1 to C10 alkyl; or pharmaceutical y acceptable salts thereof;
wherein constituents of the mobile phase preferentially interact with the stationary phase and produce an eluent stream, a first portion of which is substantially comprised of the cis isomer and a second portion of the eluent stream which is substantially comprised of the trans isomer;
(b) collecting a first portion of the eluent stream substantially comprising the cis isomer; and
(c) collecting a second portion of the effluent stream, substantially comprising the trans isomer.

* * * * *